United States Patent
Seo et al.

(10) Patent No.: US 11,427,613 B2
(45) Date of Patent: Aug. 30, 2022

(54) METHOD FOR PURIFICATION OF ALBUMIN

(71) Applicant: THERAPURE BIOPHARMA INC., Mississauga (CA)

(72) Inventors: Jin Seog Seo, Mississauga (CA); David Miller, Guelph (CA)

(73) Assignee: Evolve Biologics Inc., Mississauga (CA)

( * ) Notice: Subject to any disclaimer, the term of this patent is extended or adjusted under 35 U.S.C. 154(b) by 140 days.

(21) Appl. No.: 16/492,766

(22) PCT Filed: Mar. 16, 2018

(86) PCT No.: PCT/CA2018/050321
§ 371 (c)(1),
(2) Date: Sep. 10, 2019

(87) PCT Pub. No.: WO2018/165766
PCT Pub. Date: Sep. 20, 2018

(65) Prior Publication Data
US 2021/0139534 A1    May 13, 2021

Related U.S. Application Data

(60) Provisional application No. 62/472,007, filed on Mar. 16, 2017.

(51) Int. Cl.
*C07K 1/34* (2006.01)
*C07K 14/765* (2006.01)

(52) U.S. Cl.
CPC .............. *C07K 1/34* (2013.01); *C07K 14/765* (2013.01)

(58) Field of Classification Search
None
See application file for complete search history.

(56) References Cited

U.S. PATENT DOCUMENTS

| | | | |
|---|---|---|---|
| 2,705,230 A | 3/1955 | Reid | |
| 3,992,367 A | 11/1976 | Plan et al. | |
| 6,022,954 A | 2/2000 | Dernis et al. | |
| 2003/0187226 A1* | 10/2003 | Goodey | A61P 17/02 530/362 |
| 2004/0121316 A1 | 6/2004 | Birkus et al. | |

FOREIGN PATENT DOCUMENTS

| | | |
|---|---|---|
| CN | 105384791 B | 7/2016 |
| DE | 3019456 A1 | 12/1980 |
| JP | 57095997 A | 6/1982 |
| JP | 6-78994 A | 3/1994 |
| JP | 6-503231 A | 4/1994 |
| JP | 2007-232524 A | 9/2007 |
| JP | 2009-112319 A | 5/2009 |
| WO | 9305811 A1 | 4/1993 |

OTHER PUBLICATIONS

Aghaie et al. "Preparation of albumin from human plasma by heat denaturation method in a plasma bag" Transfusion Medicine 22: 440-445. (Year: 2012).*
FDA "Package Insert for Albumin (human) 5%" (Year: 2006).*
Leeman et al. "Proteins and antibodies in serum, plasma, and whole blood-size characterization using asymmetrical flow field-flow fractionation (AF4)" Analytical and Bioanalytical Chemistry 410:4867-4873. (Year: 2018).*
Anonymous "Tissue Properties: Low Frequency (Conductivity)" https://itis.swiss/virtual-population/tissue-properties/database/low-frequency-conductivity/. (Year: 2019).*
Burnhouf T "Modern Plasma Fractionation" Transfusion Medicine Reviews 21:101-117. (Year: 2007).*
Aghaie et al. "Preparation of albumin from human plasma by heat denaturation method in plasma bag" Transfusion Medicine 22: 440-445. (Year: 2012).*
Pansare et al. "Ultrafiltration of Protein Solutions" Chem. Eng. Ed. 49:9-17. (Year: 2015).*
Aghaie, A. et al., "Preparation of albumin from human plasma by heat denaturation method in plasma bag". Transfusion Medicine, Epub: Oct. 29, 2012, vol. 22, No. 6, p. 440-445.
Faroongsarng and Kongprasertkit. "The role of caprylate ligand ion on the stabilization of human serum albumin", AAPS PharmSciTech. Epub: Jan. 28, 2014, vol. 14, No. 2, p. 465-471.
Anderson and Anderson, "The Human Plasma Proteome: History, Character, and Diagnostic Prospects." Molecular & Cellular Proteomics, 2002, 1.11:845-867.
Japanese Notice of Reasons for Rejection for corresponding Japanese Patent Application No. 2019-550743. (English translation also provided.).
Computer English Translation of Japanese Patent Publication No. 2007-232524 A.
Computer English Translation of Japanese Patent Publication No. 6-78994.
Barth et al., "Harmonisation of Reference Intervals." Pathology Harmony Group, Clinical Biochemistry Outcomes, Jan. 2011.

* cited by examiner

*Primary Examiner* — Sudhakar Katakam
*Assistant Examiner* — Zachary J Miknis
(74) *Attorney, Agent, or Firm* — Bereskin & Parr LLP/S.E.N.C.R.L., s.r.l.; Micheline Gravelle

(57) ABSTRACT

A method for the purification of albumin from plasma is described. The method comprises (a) contacting the plasma with sodium caprylate (NaCP) at an amount dependent on total protein concentration and the ratio of NaCP to total protein in the plasma, (b) heating the plasma at a near neutral pH range, and (c) separating the albumin from non-albumin-phase. The said method provides for a high yield and purity albumin solution.

19 Claims, 36 Drawing Sheets

| Lane | Sample | Sample protein conc. (mg/mL) | Total Prot. loaded (μg) |
|---|---|---|---|
| 1 | MW | | |
| 2 | HSA Irvine standard | 100 | 0.5 |
| 3 | AAT Standard | 12.4 | 0.5 |
| 4 | 060716 SPTFF-1 | 73.24 | 10 |
| 5 | 070516 PAS1-1 | 58.73 | 10 |
| 6 | 070516 PAS2-1 | 55.67 | 10 |
| 7 | 070516 PAS3-1 | 46.91 | 10 |
| 8 | 070516 PAS4-1 | 48.63 | 10 |

| Label | Description | Purity, % |
|---|---|---|
| A | pH increase with NaOH, heated at 65 C for 4 hr | 95.80 |
| B | pH down to 5.2 with citric acid after 30 min | 97.88 |
| C | pH down to 5.2 with citric acid after 1 hr | 97.06 |
| D | pH down to 5.2 with citric acid after 2 hr | 98.28 |
| E | pH down to 5.2 with citric acid after 4 hr | 99.04 |
| F | pH down to 5.4 with citric acid after 4 hr | 98.89 |

| Lane | Sample | Sample protein conc. (mg/mL) |
|---|---|---|
| 1 | MW | |
| 2 | HSAIRVINE | 100 |
| 3 | AAT | 12.4 |
| 4 | 060716 SPTFF-1 | 72.75 |
| 5 | 070816 PAS1-1 | 57.68 |
| 6 | 070816 PAS1-2 | 42.96 |
| 7 | 070816 PAS2-1 | 63.03 |
| 8 | 070816 PAS2-2-2 | 52 |
| 9 | 070816 PAS2-2-4 | 50.68 |
| 10 | 070816 PAS2-2-5 | 52.47 |
| 11 | 070816 PAS3-1 | 58.59 |
| 12 | 070816 PAS3-2 | 44.63 |

A, non-reduced gel
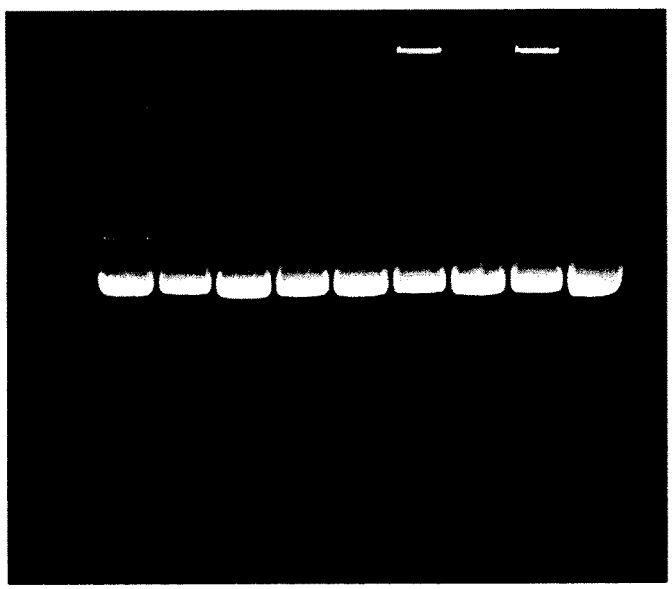
B, reduced gel
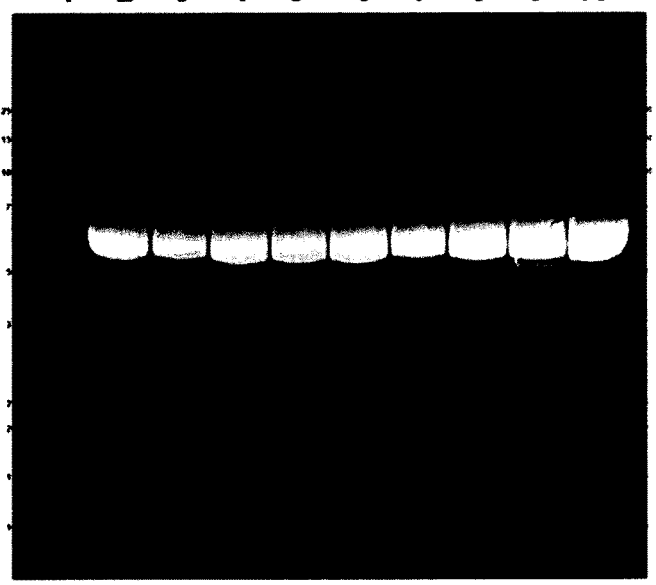
| Lane | Sample | Description |
|---|---|---|
| 1 | MW | |
| 2 | 071316 SPTFF-2 | Concentrated Col D FT+W |
| 3 | 071816 PAS1 | 70mM NaCP |
| 4 | 071816 PAS1-2 | 3 hours at 65 °C, pH 5.2 |
| 5 | 071816 PAS1-3 | PAS1-2 with 0.7% P-1000 |
| 6 | 071816 PAS1-6 | 6 hours at 65 °C 0.7% P-1000 |
| 7 | 071816 PAS2-1 | 90mM NaCP 3 hours at 65 °C |
| 8 | 071816 PAS2-6 | 6 hours at 65 °C 0.7% P-1000 |
| 9 | 071816 PAS3-1 | 110mM NaCP 3 hours at 65 °C |
| 10 | 071816 PAS3-6 | 6 hours at 65 °C 0.7% P-1000 |
FIGURE 9

| Lane | Sample | Description |
|---|---|---|
| 1 | MW | Molecular weight marker |
| 2 | HAS Irvine Standard | Standard |
| 3 | 071316 SPTFF-2 | Starting solution |
| 4 | 072616 PAS1-2 | 135mM NaCP, heated for 4 hours at 65 °C, pH 7 |
| 5 | 072616 PAS1-3 | 135mM NaCP, heated for 4 hours at 65 °C, pH 5.2 |
| 6 | 072616 PAS2-3 | 80 mM NaCP, heated for 4 hours at 65 °C, pH 5.2 |
| 7 | 072616 PAS3-3 | 67.5 mM NaCP, heated for 4 hours at 65 °C, pH 5.2 |
| 8 | 072616 PAS4-3 | 55 mM NaCP, heated for 4 hours at 65 °C, pH 5.2 |
| 9 | 072616 PAS5-3 | 40 mM NaCP, heated for 4 hours at 65 °C, pH 5.2 |
| 10 | 072616 PAS6-3 | 35 mM NaCP, heated for 4 hours at 65 °C, pH 5.2 |

| Lane | Sample | Description |
|---|---|---|
| 1 | MW | |
| 2 | HAS Irvine Standard | |
| 3 | 071316 SPTFF-2 | Concentrated Col D FT+W |
| 4 | 072616 PAS1-2 | 135mM NaCP, Pasteurized |
| 5 | 072616 PAS1-3 | After adjusting pH 5.2 |
| 6 | 072616 PAS2-3 | After adjusting pH 5.2 |
| 7 | 072616 PAS3-3 | After adjusting pH 5.2 |
| 8 | 072616 PAS4-3 | After adjusting pH 5.2 |
| 9 | 072616 PAS5-3 | After adjusting pH 5.2 |
| 10 | 072616 PAS6-3 | After adjusting pH 5.2 |

| Lane | Sample |
|---|---|
| 1 | MW |
| 2 | HSA irvine standard |
| 3 | 080916 PAS1-3 |
| 4 | 080916 PAS2-3 |
| 5 | 080916 PAS3-3 |
| 6 | 080916 PAS4-3 |
| 7 | HSA Baxter Standard |

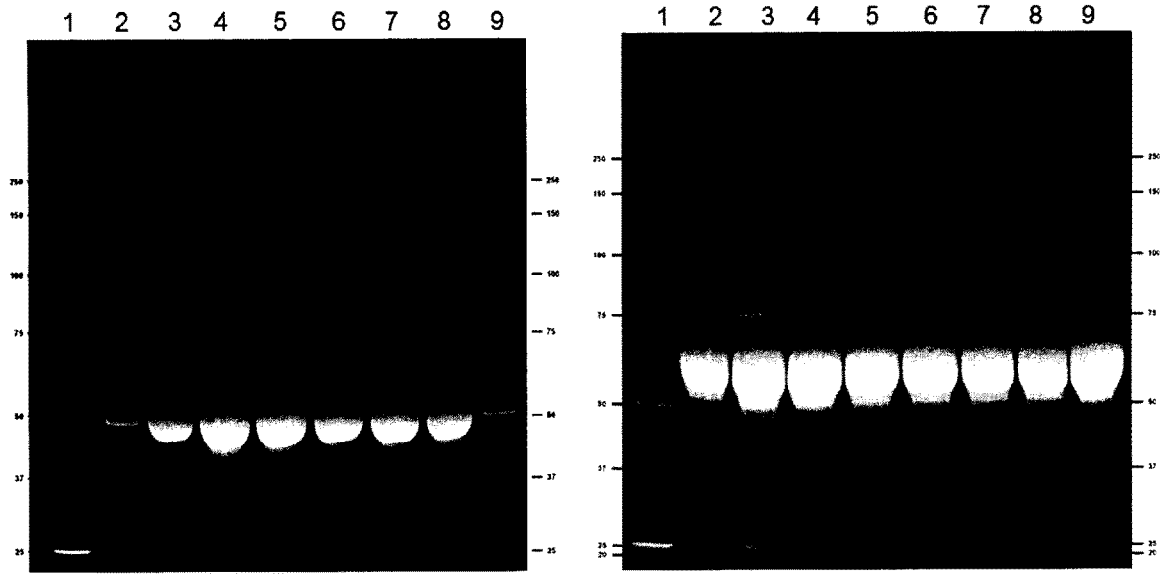

A, loading for standards was 1 µg, samples were 10 µg

B, loading was 10 µg

| Lane | Sample | Description |
|---|---|---|
| 1 | MW | Molecular weight marker |
| 2 | HSA Irvine Standard | Standard |
| 3 | 071316 SPTFF-2 | Starting solution |
| 4 | 080916 PAS1-3 | 60 mg/mL TP-65 mM NaCP, heated for 4 hours at 65 °C, 100 mL scale, citric acid to adjust pH 5.2, sample by centrifugation |
| 5 | 080916 PAS1-4 | 60 mg/mL TP-65 mM NaCP, heated for 4 hours at 65 °C, 100 mL scale, citric acid to adjust pH 5.2, sample by filtration |
| 6 | 080916 PAS2-3 | 60 mg/mL TP-65 mM NaCP, heated for 4 hours at 65 °C, 10 mL scale, citric acid to adjust pH 5.2 |
| 7 | 080916 PAS3-3 | 80 mg/mL TP-87 mM NaCP, heated for 4 hours at 65 °C, 10 mL scale, citric acid to adjust pH 5.2 |
| 8 | 072616 PAS4-3 | 80 mg/mL TP-87 mM NaCP, heated for 4 hours at 65 °C, 10 mL scale, phosphoric acid to adjust pH 5.2 |
| 9 | HSA Baxter Standard | Standard |

FIGURE 19

| Lane | Sample |
|---|---|
| 1 | MW |
| 2 | HAS Baxter Standard |
| 3 | 071316 SPTFF-2 |
| 4 | 081816 PAS5-1 |
| 5 | 081816 PAS5-3 |
| 6* | 081816 PAS6-3 |
| 7 | 081816 PAS7-3 |
| 8 | 081816 PAS8-3 |
| 9 | 081816 PAS9-3 |
| 10* | 081816 PAS10-3 |
| 11 | 081816 PAS14-3 |
| 12 | 081216 ILC |
| *The acid treated samples | |

A Reduced gel
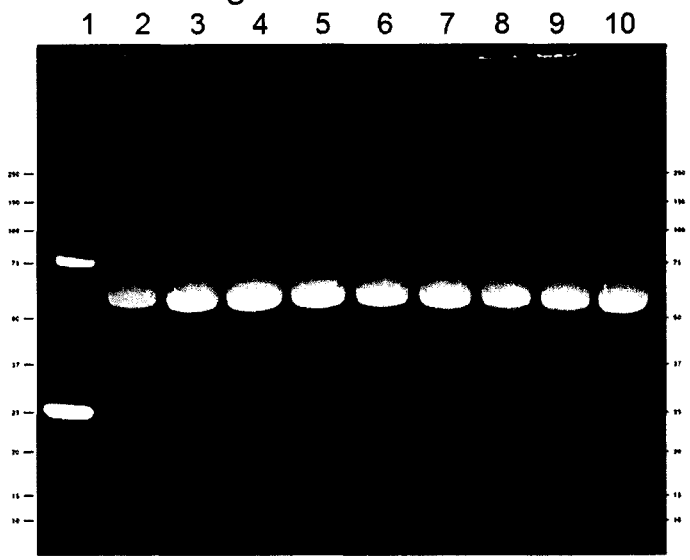
B Non-reduced gel
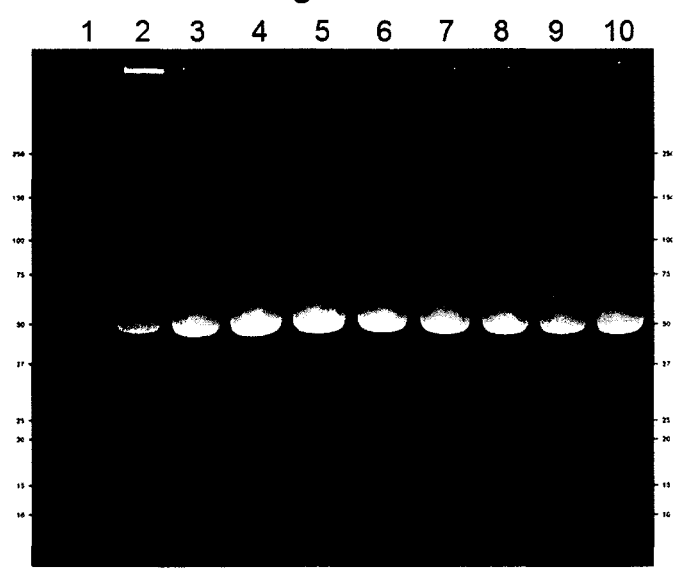
| Lane | Sample |
|---|---|
| 1 | MW |
| 2 | 092116 PAS1-1 |
| 3 | 092116 PAS1-2a |
| 4 | 092116 PAS1-2b |
| 5 | 092116 PAS1-3 |
| 6 | 092116 PAS1-4a |
| 7 | 092116 PAS1-4b |
| 8 | 092216 - MF-2 (microfiltration) |
| 9 | 092316 - ILC-1 (concentration of MF) |
| 10 | 090116 - PAS3-2 (previous sample) |
FIGURE 28

| Lane | Sample |
|---|---|
| 2 | Cryo poor plasma |
| 3 | Process intermediate before pasteurization step |
| 4 | |
| 5 | |
| 6 | |
| 7 | Before pasteurization |
| 8 | After pasteurization and clarification (via hollow fibre TFF) |

METHOD FOR PURIFICATION OF ALBUMIN

CROSS REFERENCE TO RELATED APPLICATION

This application is a national phase entry application of Patent Cooperation Treaty Application No. PCT/CA2018/050321, filed Mar. 16, 2018 (which designates the U.S.), which claims the benefit of U.S. Provisional Application No. 62/472,007, filed Mar. 16, 2017, which is are incorporated herein by reference in #s their entirety.

FIELD

The present disclosure relates to a novel method for the purification of albumin from plasma. The method involves contacting the plasma with sodium caprylate (NaCP) at an amount dependent on total protein concentration and the ratio of NaCP to total protein in the plasma, pasteurizing the plasma at a near neutral pH range, and separating the albumin from non-albumin-phase. The said method provides for a high yield and purity albumin solution.

BACKGROUND

Human and animal blood is a source of molecules that possess therapeutic properties. Many of these molecules are proteins that may be found in plasma or serum. These proteins have been the target for specific isolation with the aim of purifying and standardising the molecules for use as human therapeutic agents. For examples, albumin, immunoglobulin G, Factor VIII and alpha-1-proteinase inhibitor are all available as isolated therapeutic products.

One of the conventionally used methods for the fractionation of blood plasma or blood serum proteins has been described in U.S. Pat. No. 2,390,074 which discloses a method for the fractionation of plasma or serum proteins in large-scale by utilizing ethanol precipitation and regulating temperature, pH, ionic strength and time to control precipitation of certain proteins from human plasma. The fractionation method involves the stepwise addition of ethanol to the plasma raw material in order to obtain several fractions and corresponding supernatants comprising different enriched protein solutions.

Ethanol precipitation method suffers the drawback that some proteins tend to denature in the presence of ethanol resulting in decreased yield of the protein to be isolated and contamination with aggregates that need to be removed before an acceptable therapeutic product can be obtained. Furthermore, precipitated proteins require resolubilization for further processing which leads to significant levels of insoluble protein and lipid material that hinder the purification of the final product, resulting in further reduction in yield.

Furthermore, human serum albumin (HSA) in particular has been purified from plasma by various fractionation methods. Albumin is the most abundant protein in human blood plasma, constituting up to 60% of serum protein. Therapeutic albumin is formulated by following a pharmaceutical guideline. Under regulatory guideline, the formulation contains N-acetyl tryptophan and caprylate followed by pasteurization at 60±0.5° C. for 10.5±0.5 hour for the purpose of viral inactivation. The amount of both reagents as stabilizer is determined based on the amount of HSA, which is set at 0.08±0.016 mmol/g-HSA protein.

The integrity of HSA is maintained during the pasteurization by the presence of the caprylate/tryptophan regimen. The caprylate ion is believed to decrease the rate of reversible partial unfolding by binding to HSA, thereby inhibiting one step in the pathway which leads to irreversible precipitation. Faroongsarng and Kongprasertkit (2014) observed that the denaturing temperature of HSA increases from 67.23° C. to 72.85° C. in the presence of 0.08 mmol NaCP per gram of HSA.

The basic concept and prior art in the field of albumin isolation have been described, for examples, in U.S. Pat. Nos. 2,705,230, 3,992,367, 4,156,681, 5,118,794, 6,022,954, and 6,504,011. These documents are incorporated herein by reference.

U.S. Pat. No. 6,022,954 relates to a process for preparing purified albumin from a human or animal physiological solution, such as plasma or a plasma fraction. This document teaches a process of delipidation using an anionic detergent and two chromatographic separation stages using ion-exchange resin. The delipidation treatment consists of contact of the albumin solution from the first chromatography stage for approximately 1 hour at 60° C. with a detergent and in the presence of low amount of NaCP as a stabilizer. The pasteurization treatment consists of heating the solution at over 60° C. for at least 10 hours.

U.S. Pat. No. 5,118,794 relates to a process for stabilizing human albumin during heat treatment in a container which involves the addition of a surfactant agent. This document discloses a process that involves pasteurizing the solution with low amount of NaCP, at an amount of 0.08-0.64 mmol NaCP per gram of albumin, at pH 7.0. This document further discloses final pasteurization of the product at 60° C. for 10 hours.

In U.S. Pat. No. 3,992,367, the process of albumin purification involves a heating step where the solution consists of NaCP in weight between 15% and 30% at a pH between 4.8 and 5.25. In U.S. Pat. No. 2,705,230, albumin isolation involves pasteurization heat treatment that was carried out at pH 8 using 50 and 500 mM NaCP.

U.S. Pat. No. 4,156,681 relates to a method for abstracting serum albumin from blood which includes the steps of separating the blood plasma from the solid constituents of the blood, isolating the dissolved non-albumin constituents from plasma, and adding an albumin-stabilizer and treating such fluid with a lower aliphatic alcohol. The method involves adding low amount of NaCP to a large volume of plasma for albumin purification and carrying out the heat treatment at a pH between 4.5 and 7.5.

U.S. Pat. No. 6,504,011 relates to a process for purifying recombinantly produced serum albumin by incubation with an anion exchange adsorbent, followed by affinity chromatography employing a hydrophobic solid phase and using a water soluble lipid anion as desorbens in the aqueous phase. This document teaches albumin purification by chromatography without a pasteurization stage and the use of NaCP in an elution buffer for the recovery of albumin.

Previous reports did not lend themselves to understand the complex relationship between total protein concentration and the ratio of NaCP to total protein in the plasma during pasteurization for the purification of albumin. The high yield and purity achieved by the presently disclosed method provides an advantage in maximizing the quality and quantity of recovered albumin.

SUMMARY

The present disclosure describes an improved method for the purification of albumin from plasma.

Accordingly, the present disclosure provides a method for purifying albumin from plasma comprising:

(a) contacting the plasma with sodium caprylate (NaCP), wherein the amount of NaCP is between 0.1 and 5 mmol NaCP per gram of total protein in the plasma;

(b) heating the plasma at a temperature between 60 and 70° C.; and (c) separating the albumin from the non-albumin phase.

In one embodiment, the plasma is concentrated prior to step (a) to a total protein concentration between 20 and 150 g/L, preferably between 45 and 65 g/L.

In another embodiment, the amount of NaCP is between 0.2 and 3, optionally between 0.5 and 2, optionally between 0.8 and 1.3 mmol NaCP per gram of total protein.

In another embodiment, the NaCP added is in a concentration between 20 and 140 mM, optionally between 40 and 100 mM, optionally between 50 and 90 mM, optionally between 60 and 85 mM.

In another embodiment, the heating of the plasma in step (b) is carried out at a pH between 6.0 and 8.0, optionally between 6.5 and 7.5, optionally between 6.7 and 7.3, optionally between 6.7 and 6.9.

In another embodiment, the conductivity of the plasma is less than 9 mS/cm, optionally less than 5 mS/cm.

In another embodiment, the heating of the plasma is carried out at a temperature between 60 and 70° C., optionally between 62 and 65° C., for a period between 0.5 and 24 hours, optionally between 2 and 12 hours, optionally between 3 and 12 hours, optionally between 4 and 6.5 hours.

In another embodiment, the separation of the albumin from the non-albumin phase in step (c) comprises precipitation of non-albumin protein and lipid impurities.

In another embodiment, the separation of the albumin from the non-albumin phase comprises cooling the plasma to below 30° C.

In another embodiment, the plasma is filtered in step (c), optionally through a Pall Seitz K700P depth filter in the presence of Harborlite filter aid (2% w/v H900, 2% w/v H1900), tangential flow filtration (TFF) with a cassette, or hollow fibre TFF, preferably hollow fibre TFF.

In another embodiment, the separation of the albumin from the non-albumin phase comprises adjusting the pH of the plasma to between 4.8 and 5.4, optionally between 5.1 and 5.3.

In another embodiment, the adjustment of the pH of the plasma is carried out by the addition of acid.

In another embodiment, the method for purification of albumin can be linearly scalable.

In addition, the present disclosure includes a recovered albumin solution with an albumin content of at least 90% (w/w) of protein, optionally at least 92% (w/w) of protein, optionally at least 94% (w/w) of protein, optionally at least 96% (w/w) of protein, optionally at least 98% (w/w) of protein, optionally at least 99% (w/w) of protein.

Other features and advantages of the present disclosure will become apparent from the following detailed description. It should be understood, however, that the detailed description and the specific Examples while indicating preferred embodiments of the disclosure are given by way of illustration only, since various changes and modifications within the spirit and scope of the disclosure will become apparent to those skilled in the art from this detailed description.

BRIEF DESCRIPTION OF THE DRAWINGS

The disclosure will now be described in relation to the drawings in which:

FIG. 9 shows non-reduced and reduced SDS-PAGE gels.

FIG. 19 shows a SDS-PAGE gel, 7.5% Invitrogen Gel (200 V×22 minutes).

FIG. 28 shows non-reduced and reduced gel of the samples.

DETAILED DESCRIPTION

Figure 1:
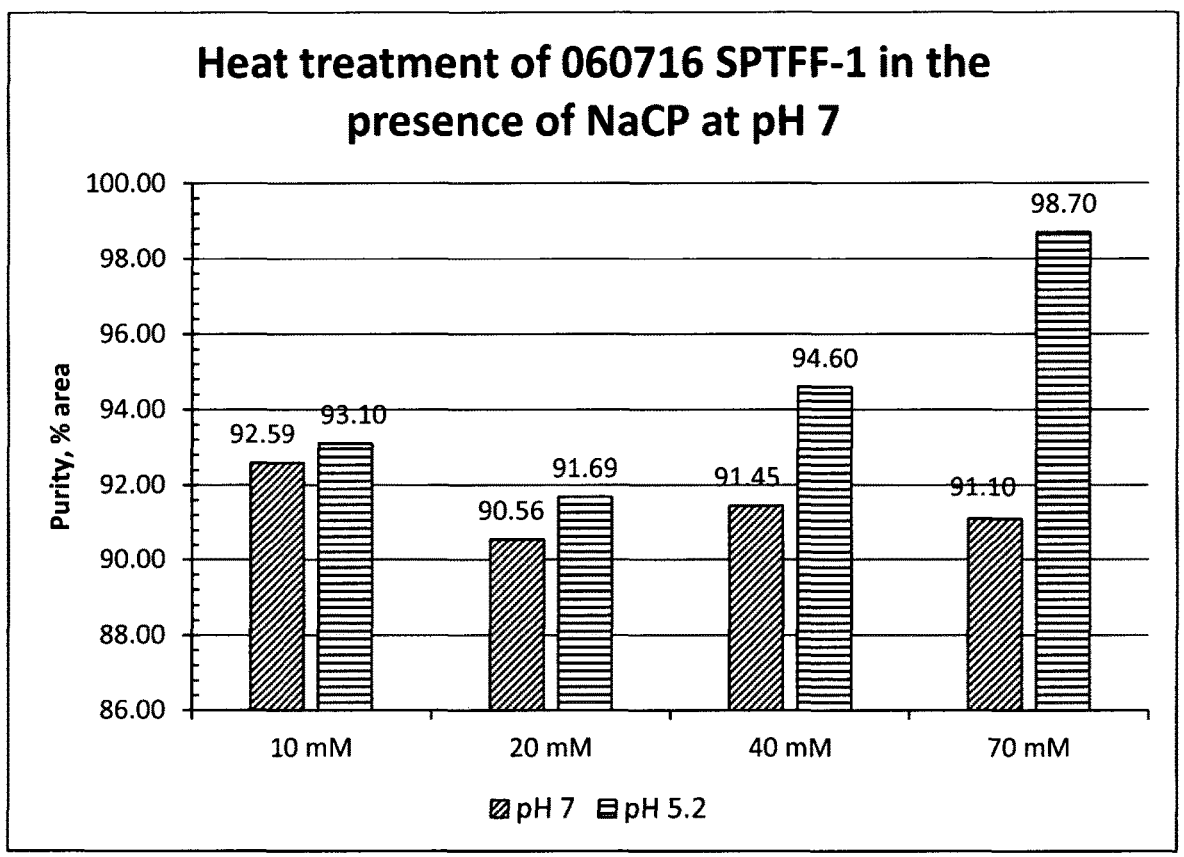
FIG. 1 shows an illustration of purities and recoveries of HSA after each purification step.

HSA was purified from plasma and partially fractionated plasma by using NaCP at a concentration dependent on total protein concentration and the amount of NaCP per gram of total protein in the plasma, at near neutral pH, followed by separation of albumin and non-albumin phase by cooling and decreasing the pH of the pasteurized plasma. The purification process was carried out without the use of ethanol or extensive processing steps. The final recovered HSA is of high yield at exceptional purity.

Accordingly, the present disclosure provides a method for purifying albumin from plasma comprising:
(a) contacting the plasma with sodium caprylate (NaCP), wherein the amount of NaCP is between 0.1 and 5 mmol NaCP per gram of total protein in the plasma;
(b) heating the plasma at a temperature between 60 and 70° C.; and
(c) separating the albumin from the non-albumin phase.

Unless otherwise indicated, the definitions and embodiments described in this and other sections are intended to be applicable to all embodiments and aspects of the present disclosure herein described for which they are suitable as would be understood by a person skilled in the art.

In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. The term "consisting" and its derivatives, as used herein, are intended to be closed terms that specify the presence of the stated features, elements, components, groups, integers, and/or steps, but exclude the presence of other unstated features, elements, components, groups, integers and/or steps. The term "consisting essentially of", as used herein, is intended to specify the presence of the stated features, elements, components, groups, integers, and/or steps as well as those that do not materially affect the basic and novel characteristic(s) of features, elements, components, groups, integers, and/or steps.

As used herein, the singular forms "a", "an" and "the" include plural references unless the content clearly dictates otherwise. In embodiments comprising an "additional" or "second" component, the second component as used herein is different from the other components or first component. A "third" component is different from the other, first, and second components, and further enumerated or "additional" components are similarly different.

In the absence of any indication to the contrary, reference made to a "%" content throughout this specification is to be taken as meaning % w/v (weight/volume).

As used herein, the term "purified" and its derivatives is meant purified from other common components present in plasma, fractionated plasma, cryo poor plasma, plasma intermediate, solution of plasma proteins, or mixtures thereof. For example, purified albumin is purified away from the other proteins, nucleic acids, lipids and small metabolites present in plasma fractionated plasma, cryo poor plasma, plasma intermediate, solution of plasma proteins, or mixtures thereof. A purified albumin is at least 60% pure by weight, optionally at least 75%, 80%, 85%, 90%, 92%, 95%, 96%, 97%, 98%, 99%, 99.5%, 99.9% or even 100% pure, from other proteins, nucleic acids, lipids, or small metabolites present in plasma, partially fractionated plasma, cryo poor plasma, plasma intermediate, solution of plasma proteins, or mixtures thereof.

As used herein, the term "plasma" and its derivatives includes partially fractionated plasma, cryo poor plasma, plasma intermediate, solution of plasma proteins, or mixtures thereof. It is readily apparent to the person skilled in the art how to obtain partially fractionated plasma, cryo poor plasma, plasma intermediate, solution of plasma proteins, or mixtures thereof. For example, partially fractionated plasma may be prepared from filtration through Seitz® EK1 filter (0.45-0.65 μm).

The method of the disclosure may in principle be used for purifying any known albumin such as albumin derived from human, non-human primate, sheep, goat, bovine, donkey, canine, feline, rabbit, rodent, hamster, guinea pig and fowl.

The total protein in the plasma can be concentrated prior to the addition of the NaCP. The concentration can be done using techniques known in the art including the addition of water or any suitable buffer known to a person skilled in the art. The NaCP is preferably added to the plasma at a pH range of 6.6 to 7.2, most preferably at a pH range of 6.7 to 6.9.

It is important to regulate the total protein in the plasma. In particular, the total protein in the plasma should be in a concentration between 20 and 150 g/L, such as at least 20, 25, 30, 35, 40, 45, 50, 55, 60, 65, or 70 g/L, and at most 45, 50, 55, 60, 65, 70, 75, 80, 85, 90, 95, 100, 105, 110, 115, 120, 125, 130, 135, 140, 145, or 150 g/L. In a specific embodiment, the total protein is in a concentration between 35 and 80 g/L, or 45 and 65 g/L.

Regulating the amount of NaCP used is an important aspect of the method. In particular, the amount of NaCP is between 0.1 and 5 mmol NaCP per gram of total protein in the plasma, such as at least 0.1, 0.2, 0.3, 0.4, 0.5, 0.6, 0.65, 0.66, 0.67, 0.68, 0.69, 0.7, 0.75, 0.8, 0.85, 0.9, 0.95, 1, 1.1, 1.05, 1.15, 1.2, 1.3 or 1.4 mmol NaCP per gram of total protein in the plasma, and at most 0.9, 0.95, 1, 1.05, 1.1, 1.15, 1.2, 1.3, 1.4, 1.5, 1.6, 1.8, 2, 2.5, 3, 3.5, 4 or 5 mmol NaCP per gram of total protein in the plasma. In a specific embodiment, the amount of NaCP is between 0.2 and 3, 0.5 and 2, or 0.8 and 1.3 mmol NaCP per gram of total protein in the plasma. It is readily apparent to the person skilled in the art that the values may be converted and expressed in terms of weight, molar amount, concentration including molarity, or a combination thereof.

In another embodiment, the NaCP is added in a concentration between 20 and 140 mM, such as at least 20, 25, 30, 35, 40, 45, 50, 55, 60, 65, 70, 80, or 85 mM, and at most 65, 70, 80, 85, 90, 95, 100, 105, 110, 115, 120, 125, 130, 135, or 140 mM. In a specific embodiment, the NaCP is in a concentration between 40 and 100 mM, 50 and 90 mM, or 60 and 85 mM.

After the NaCP is added the plasma is heat treated or pasteurized. The pasteurization or heating process of the plasma is carried out at a temperature of between 60 and 70° C., such as at least 60, 61, 62, 63, 64, 65, 66, or 67° C., and at most 64, 65, 66, 67, 68, 69, or 70° C. In a specific embodiment, the pasteurization or heating process of the plasma is carried out at a temperature between 60 and 65° C., or 62 and 65° C. It is readily apparent to the person skilled in the art how to regulate the temperature, for example, by using a pasteurizer.

The pasteurization or heating process of the plasma is preferably carried out at a pH of between 6.0 and 8.0, such as at least 6.0, 6.5, 6.6, 6.7, 6.8, 6.9 or 7.0 and at most 6.7, 6.7, 6.8, 6.9, 7.0, 7.1, 7.2, 7.3, 7.5 or 8.0. In a specific embodiment, the pasteurization or heating process of the plasma is carried out at a pH between 6.5 and 7.5, 6.7 and 7.3, or 6.7 and 6.9.

The conductivity of the plasma may also be an important factor in the process. In one embodiment, the conductivity is less than 9, 8, 7, 6, 5, 4, 3, 2 or 1 mS/cm. The conductivity of the plasma may be measured by an electrical conductivity (EC) meter.

The pasteurization or heating process of the plasma is preferably carried out for between 0.5 and 24 hours, such as at least 0.5, 1, 2, 3, 4, 5 or 6 hours, and at most 5, 6, 6.5, 7, 8, 9, 10, 11, 12, 16, 20 or 24 hours. In a specific embodiment, the pasteurization or heating process of the plasma is carried out for a period between 0.5 and 12 hours, 2 and 12 hours, 3 and 12 hours, or 4 and 6.5 hours.

In a specific embodiment, the pasteurization or heating process of the plasma is carried out at a temperature between 62 and 65° C., for a period between 4 and 6.5 hours.

In a specific embodiment, the pasteurization or heating process of the plasma is carried out at a pH between 6.7 and 6.9 at a temperature between 62 and 65° C. for a period of at least 4 hours, wherein amount of NaCP is between 0.8 and 1.3 mmol NaCP per gram of total protein, wherein the total protein is in a concentration between 45 and 65 g/L.

In step (c), the albumin is separated from the non-albumin proteins in the plasma. The separation of the albumin from the non-albumin phase involves precipitation of non-albumin protein and lipid impurities. In a specific embodiment, the separation of the albumin from the non-albumin phase involves cooling the pasteurized plasma to below 30° C.

In another embodiment, the separation of the albumin from the non-albumin phase involves adjusting the pH of the plasma to between 4.8 and 5.4, such as 4.8, 4.9, 5.0, 5.1, 5.2, 5.3 or 5.4. In a specific embodiment, the separation of the albumin from the non-albumin phase involves adjusting the pH to between 4.9 and 5.3, optionally between 5.1 and 5.3. It would be readily apparent to the person skilled in the art to employ filter aid for the separation step, including the addition of filter aid such as Celpure® P1000, Celpure® P300, or a mixture thereof to the pasteurized plasma prior to filtration (i.e. separation of albumin from non-albumin through filtration).

In an aspect, the separation of albumin from non-albumin can be carried out over a depth filter, tangential flow filtration (TFF) with a cassette, or hollow fibre TFF. Hollow fibre cross flow filters are open channel devices that are ideal for use with liquids that are turbid and can handle solids concentrations up to 40% (v/v). Hollow fibre filters are less sensitive to variability in levels of particles/colloids/cells, or liquids that are viscous or become viscous upon concentration. These filters are often chosen when product recovery from the filter is important (for example vaccine processes). Since hollow fibre filters have a smooth and unobstructed internal flow path, they are ideal for recovery of product from the filter. They are available in different flow path geometries (nominal fibre diameters from 0.5 to 1.75 mm inner diameter (ID) with nominal fibre length options of 30, 60 or 110 cm length). A person skilled in the art would appreciate that variances of hollow fibre TFF can alternatively be used for separating albumin from non-albumin.

Cassettes are most often used for concentration and diafiltration of "clear" low viscosity fluids. The use of screen type turbulence promoters, enhances de-polarization of solute at the membrane surface, increasing sample flux. Under the same process conditions, pore size and filter area, cassette may have up to 2× the flux of a hollow fibre filter. However, cassettes are not suitable for solutions containing particles, colloidal suspensions or have high viscosity, due to the "plugging"/pressure drop of the screen spacers.

In an embodiment, the separation of albumin from non-albumin comprises filtration or clarification over a depth filter, tangential flow filtration (TFF) with a cassette, or hollow fibre TFF, preferably hollow fibre TFF. In an embodiment, the separation of the albumin from the non-albumin phase by depth filter, TFF with a cassette, or hollow fibre TFF is carried out at pH between 4.8 and 5.4, optionally between 5.1 and 5.3. In another embodiment, the separation of albumin from non-albumin through filtration or clarification is carried out at feed flow between 1, 2, 3, 4, or 5, and 6, 7, 8, 9, or 10 L/min per m², optionally between 1 and 10 L/min per m², optionally between 2 and 10 L/min per m², optionally between 3 and 10 L/min per m², optionally between 8 and 9 L/min per m². In another embodiment, the separation of albumin from non-albumin through filtration or clarification is carried out with between 1× and 1.2× initial volume reduction concentration, preferably 1.2×, and between 3 and 4 diavolumes, preferably 4 diavolumes. In an embodiment, the separation of albumin from non-albumin comprises filtration or clarification is carried out with hollow fibre TFF at pH between 4.8 and 5.4, optionally between 5.1 and 5.3, at feed flow between 3 and 10 L/min per m², optionally between 8 and 9 L/min per m². In a specific embodiment, the separation of albumin from non-albumin comprises filtration or clarification is carried out with hollow fibre TFF at pH between 4.8 and 5.4, optionally between 5.1 and 5.3, at feed flow between 3 and 10 L/min per m², optionally between 8 and 9 L/min per m², with initial volume reduction concentration between 1× and 1.2×, optionally 1.2×, and between 3 and 4 diavolumes, optionally 4 diavolumes.

The adjustment of the pH of the plasma may be carried out by the addition of acid, such as an organic and/or inorganic acid. In a specific embodiment, the organic acid is selected from citric acid, acetic acid and trifluoroacetic acid. In another specific embodiment, the organic acid is acetic acid. In a further embodiment, the inorganic acid is selected from hydrochloric acid, sulfuric acid and phosphoric acid.

The plasma can be filtered through a Pall Seitz K700P depth filter in the presence of Harborlite filter aid (2% w/v H900, 2% w/v H1900). It is readily apparent to the person skilled in the art how to assess the purity of the resulting albumin solution. For instance, size-exclusion chromatography-HPLC (SEC-HPLC) or capillary electrophoresis-SDS (CE-SDS) analysis may be carried out to assess the purity of albumin.

The method for purification of albumin recovers at least 40, 50, 60, 70, 75, 80, 85, 86, 87, 88, 89, 90, 91, 92, 93, 94, 95, 96, 97, 98 or 99% of albumin from the plasma.

In another embodiment, the method for purification of albumin can be linearly scalable.

In addition, the present disclosure includes an albumin solution with an albumin content of at least 90%, 92%, 95%, 96%, 97%, 98%, 99%, 99.5%, or 99.9% (w/w) of protein obtained by the method disclosed herein.

The following non-limiting Examples are illustrative of the present disclosure:

Example 1

Materials

Starting solution: Plasma, partially fractionated plasma (e.g. plasma that is IgG depleted either using Cohn fractionation or expanded bed adsorption chromatography).

NaCP: sodium caprylate, 0.6 M stock solution, pH 7.5; Acid: 0.5 M-1 M stock solution; P300: Celpure® P300 filter aid; P1000: Celpure® P1000 filter aid; NaOH: 1 M stock solution; Water: WFI; pH meter: Mettler Toledo; Depth filter: Pall Seitz® K700 Depth filter; and Glass fibre filter: Pall Seitz® (10 μm).

Pasteurization of the Column D FT+W Concentrate in the Presence of NaCP

Column D FT+W concentrated solution was mixed with NaCP, adjusted to pH 7, and then heated at 60° C. The heated solution was cooled down to room temperature and the pH was then adjusted to 5.2 using citric acid.

The total protein concentration (060716 SPTFF-2) was assumed to be approximately 1.1 mM. The total protein concentration was estimated by using albumin molecular weight (66,500 Da) because the albumin proportion was approximately 75% area by SEC HPLC while other protein proportion was not clearly addressable yet even though the impurities are mostly higher molecular weights from 100 kDa to 1,500 kDa. The total protein concentration (73 g/L) was divided by 66,500 g/mol, arriving at the value 1.1 mM.

Figure 2:
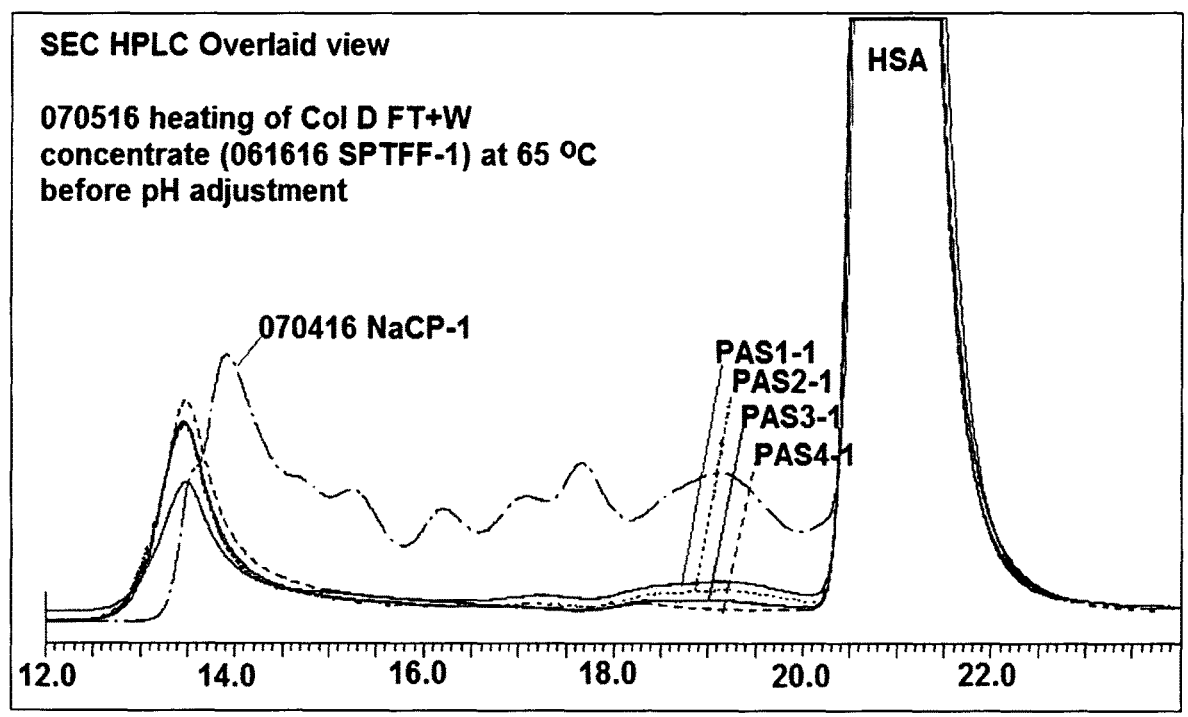
FIG. 2 shows size exclusion chromatography chromatograms of the heated samples.
Figure 3:
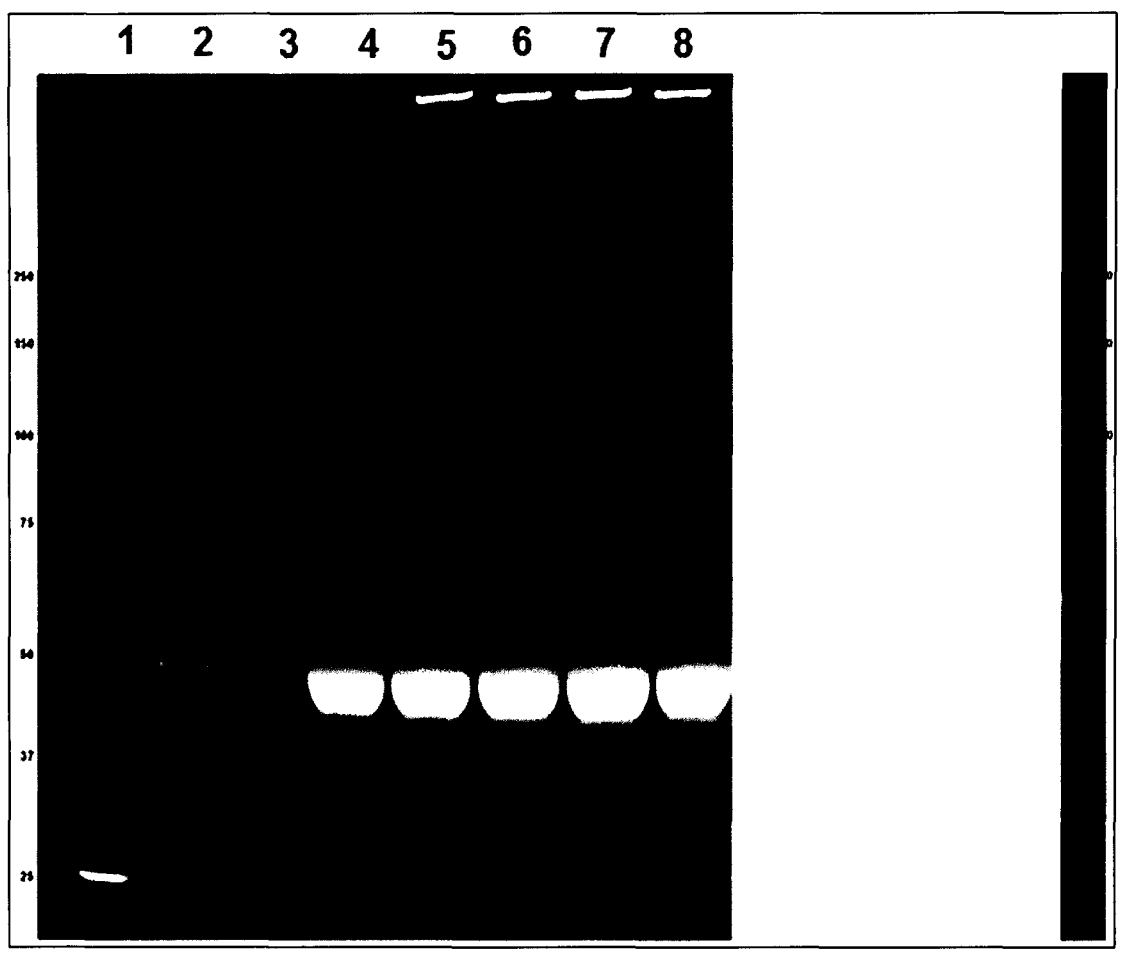
FIG. 3 shows a non-reduced SDS-PAGE gel.

The tested concentrations of NaCP were 10, 20, 40 and 70 mM NaCP, respectively. The actual concentration of total protein and NaCP was diluted during the pasteurization because the solution was pH adjusted with NaOH solution. The pH adjustment to 5.2 with citric acid was performed after pasteurization for 4 hours at 65° C. Sample preparation is summarized in Table 1. The result of the experiment was expressed as the purity of HSA based on SEC HPLC analysis (Tables 2 and 3, and FIGS. 1 and 2). FIG. 2 shows that the higher molecular weight impurities shifted the aggregates retention time (13 min) after forming a liposome or micelle. The amount of lipids was reduced after pH adjustment (Table 4). Gel analysis of samples pasteurized for 4 hours as 65° C. was also performed (FIG. 3).

TABLE 1

Experimental design for pasteurization of column D FT + W in the presence of NaCP.

| Sample code | Sample sub-number | Description |
| --- | --- | --- |
| 070516 PAS# | 1 | 060716 SPTFF-1 with NaCP after 4 hours at 65° C. |
| 070516 PAS# | 1 | Adjust the PAS#-1 solution to pH 5.2 with citric acid |

TABLE 2

NaCP/total protein ratios.

| Sample | Conc of NaCP, mM | Total Protein, mM | NaCP/[TP] | Estimated HSA, mM | NaCP/HSA |
| --- | --- | --- | --- | --- | --- |
| 070516 PAS1 | 10 | 1.1 | 9.1 | 0.938 | 12.1 |
| 070516 PAS2 | 20 | 1.1 | 18.2 | 0.938 | 24.2 |
| 070516 PAS3 | 40 | 1.1 | 36.4 | 0.938 | 48.5 |
| 070516 PAS4 | 70 | 1.1 | 63.6 | 0.938 | 84.8 |

TABLE 3

Purity of HSA.

| | After pasteurization at pH 7 | After pH adjusted to 5.2 |
| --- | --- | --- |
| sub-number | 1 | 2 |
| Sample | Purity | |
| 070516 PAS1 | 92.59 | 93.1 |
| 070516 PAS2 | 90.56 | 91.69 |
| 070516 PAS3 | 91.45 | 94.6 |
| 070516 PAS4 | 91.10 | 98.7 |

TABLE 4

Result of the lipid analysis.

| Sample | After pasteurization at pH 7 | After pH adjusted to 5.2 |
| --- | --- | --- |
| sub-number | 1 | 2 |
| Sample | Lipid concentration (ug/mL) | |
| 070516 PAS2 | 1091.5 | 91.5 |
| 070516 PAS3 | 1092.3 | 50 |
| 070516 PAS4 | 1207.1 | 40 |

Conclusion

The presence of NaCP during pasteurization removed higher molecular weight impurities from the column D FT+W concentrate. Lipid concentration decreased more than 10 times after pH adjustment of the pasteurized sample. Increased NaCP concentration reduced more lipids from the solution. Notably, as the ratio of NaCP/TP increased, the purity of HSA also increased. The best purity was obtained from 70 mM NaCP (NaCP/TP=63.6). The purity was increased from 75% to 91% after pasteurization of the solution. Adjusting pH 5.2 precipitated the impurities and increased the purity to more than 98.7%. Increased NaCP amount also increased the purity.

Example 2

Pasteurization of Column D FT+W Concentrate in the Presence of NaCP—Increased NaCP Concentration and Variable Pasteurization Time Three different concentrations of NaCP to a final concentration of 50, 70 and 90 mM NaCP in solution before pH adjustment were used. The solutions were then adjusted to pH 7, followed by pasteurization at 60-65° C. The pasteurization for 50 mM and 90 mM NaCP condition was for 4 h and then the pH was adjusted with citric acid. The 70 mM NaCP condition was aliquoted at 0.5, 1, 2 and 4 h prior to pH adjustment.

Figure 4:
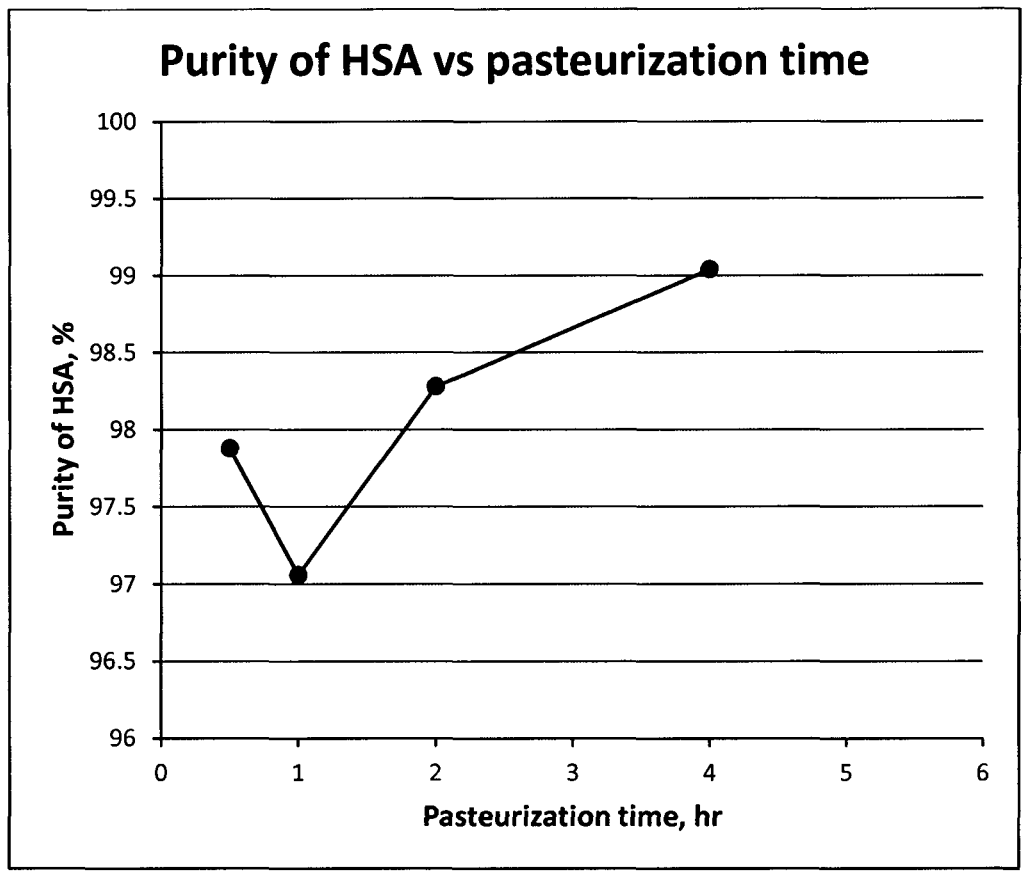
FIG. 4 shows HSA purity as a function of pasteurization time.
Figure 5:
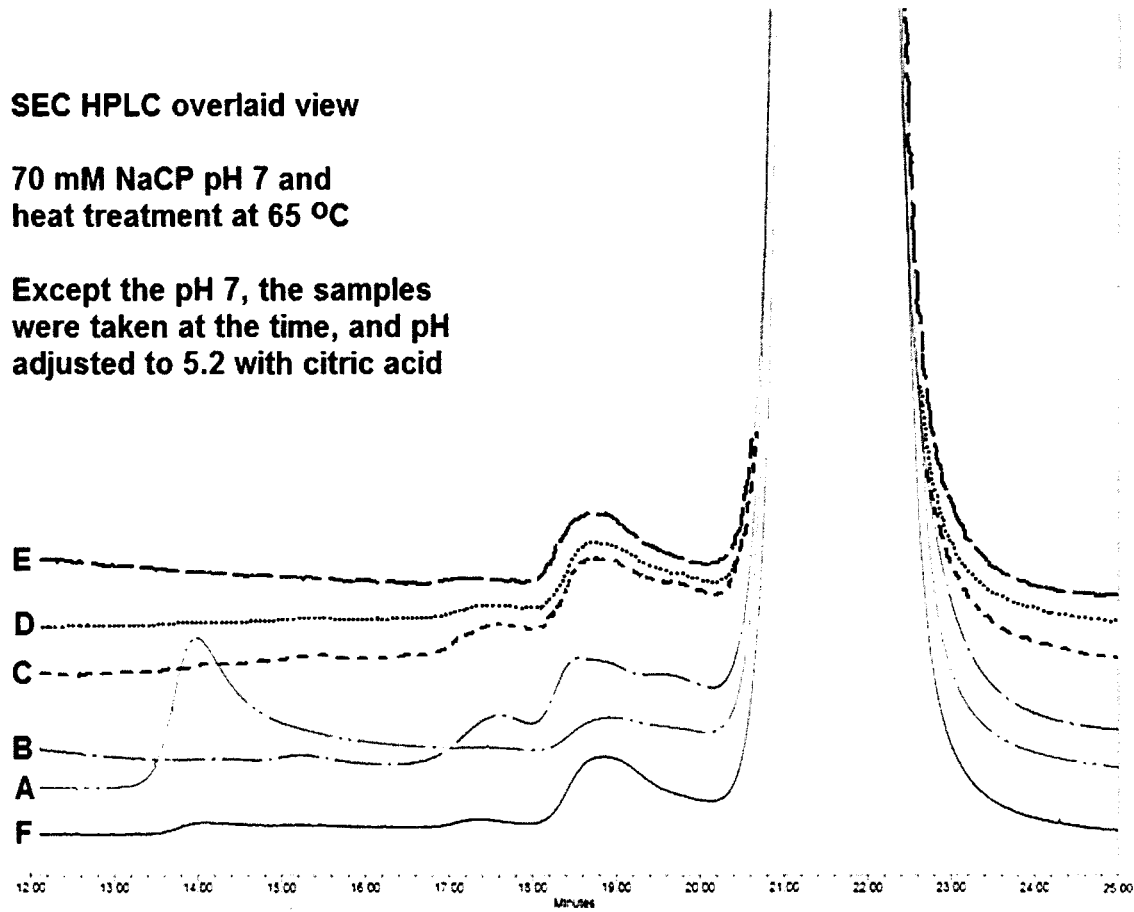
FIG. 5 shows size exclusion chromatography chromatograms of the PAS2 samples at each pasteurization time.
Figure 6:
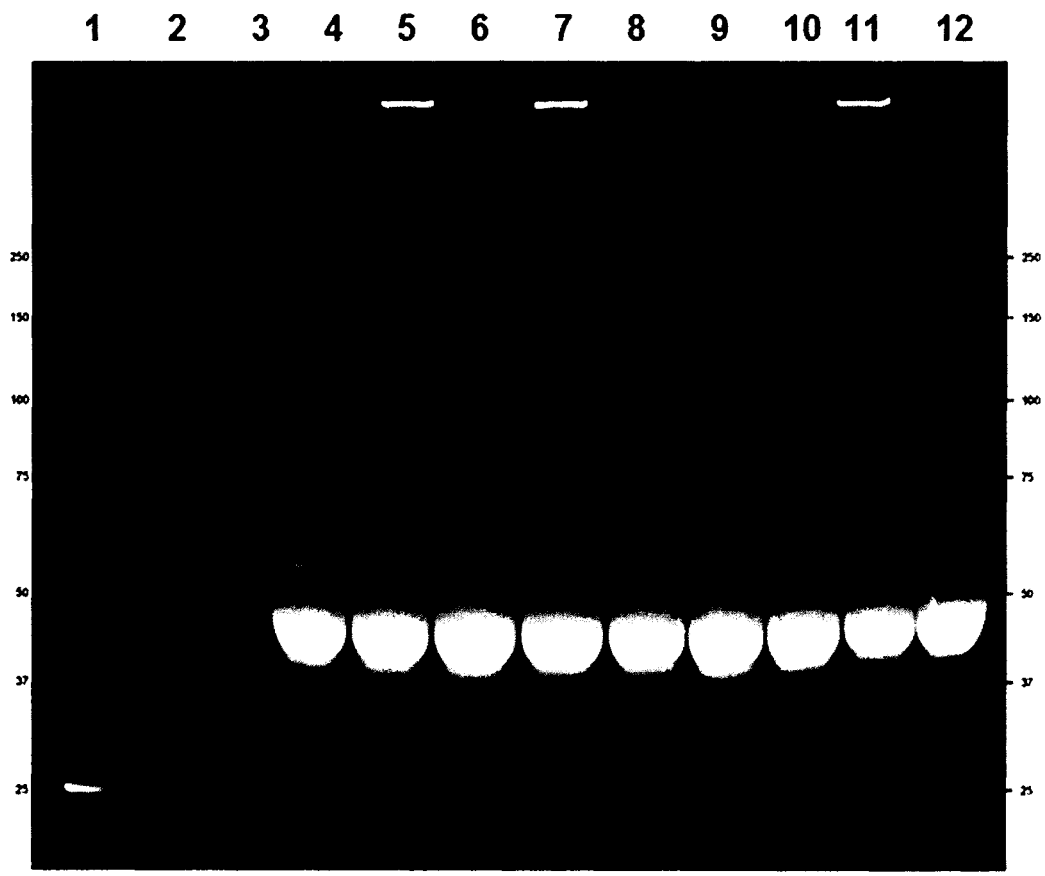
FIG. 6 shows a non-reduced SDS-PAGE gel.

The total protein concentration (060716 SPTFF-2) was assumed to be approximately 1.1 mM. The ratios of NaCP/total protein were 45.5, 63.6 and 81.8, for 50, 70 and 90 mM NaCP, respectively. Sample preparation is summarized in Tables 5 and 6. The result of the experiment was expressed as purity of HSA based on SEC HPLC analysis (Table 7, and FIGS. 4 and 5). Table 7 shows that incomplete precipitation may occur if pH adjustment was stopped at higher pH (see: sub-number 5: 4 h pH 5.4). FIG. 5 shows that at higher pH (5.4), more impurities remained, compared to pH 5.2 at 4 h pasteurization. Gel analysis of the samples was also performed (FIG. 6). As the concentration of NaCP increased, the band at 55 kDa disappeared (lane 12). A comparison of before and after pH adjustment showed the removal of aggregates and higher molecular weight impurities.

TABLE 5

Experiment for three different NaCP concentrations to a fixed total protein concentration. pH was adjusted with citric acid.

| Sample code | Conc of NaCP, mM | Description |
| --- | --- | --- |
| 070816 PAS1-1 | 50 | Pasteurization for 4 hours at 65° C. |
| 070816 PAS1-2 | 50 | Adjust the PAS1-1 solution to pH 5.2 |
| 070816 PAS2-1 | 70 | Pasteurization for 4 hours at 65° C. |
| 070816 PAS2-2-1 | 70 | Pasteurization for 0.5 hours at 65° C. and then pH adjusted 5.2 |
| 070816 PAS2-2-2 | 70 | Pasteurization for 1 hours at 65° C. and then pH adjusted 5.2 |
| 070816 PAS2-2-3 | 70 | Pasteurization for 2 hours at 65° C. and then pH adjusted 5.2 |
| 070816 PAS2-2-4 | 70 | Pasteurization for 4 hours at 65° C. and then pH adjusted 5.2 |
| 070816 PAS2-2-5 | 70 | Pasteurization for 4 hours at 65° C. and then pH adjusted 5.4 |
| 070816 PAS3-1 | 90 | Pasteurization for 4 hours at 65° C. |
| 070816 PAS3-2 | 90 | pH adjusted 5.2 |

TABLE 6

NaCP/total protein ratios.

| Sample | Conc of NaCP, mM | Total Protein, mM | NaCP/[TP] |
| --- | --- | --- | --- |
| 071816 PAS1 | 50 | 1.1 | 45.5 |
| 071816 PAS2 | 70 | 1.1 | 63.6 |
| 071816 PAS3 | 90 | 1.1 | 81.8 |

TABLE 7

Result of effects of pasteurization time on purity of HSA.

| | 0.5 h | 1 h | 2 h | 4 h | 4 h pH 5.4 |
| --- | --- | --- | --- | --- | --- |
| | sub-number | | | | |
| | 1 | 2 | 3 | 4 | 5 |
| 071816 PAS2 | 97.88 | 97.06 | 98.28 | 99.04 | 98.89 |

Conclusion

The ratio of NaCP vs total protein (TP) showed that when the ratio of NaCP/TP increased, the purity of HSA also increased. The highest purity was obtained from 90 mM NaCP (NaCP/TP=81.8). The minimum pasteurization period to recover high purity HSA was at least 4 hours. Adjusting the pH to 5.2 after pasteurization also increased the purity. If pH adjustment stopped at 5.4, the resulting HSA purity was lower.

Example 3

Ratios of NaCP Vs Total Protein—Three NaCP Concentrations to a Fixed Concentration of Total Protein Three different concentrations of NaCP to a final concentration of 70, 90 and 110 mM NaCP in solution before pH adjustment were used. The solutions were then adjusted to pH 7, followed by pasteurization at 60-65° C. Aliquots were taken at 3 and 6 h and the pH was adjusted to 5.2 with citric acid. The pH adjusted samples were mixed with P-1000 filter agent (0.7% final) before centrifugation.

Figure 7:
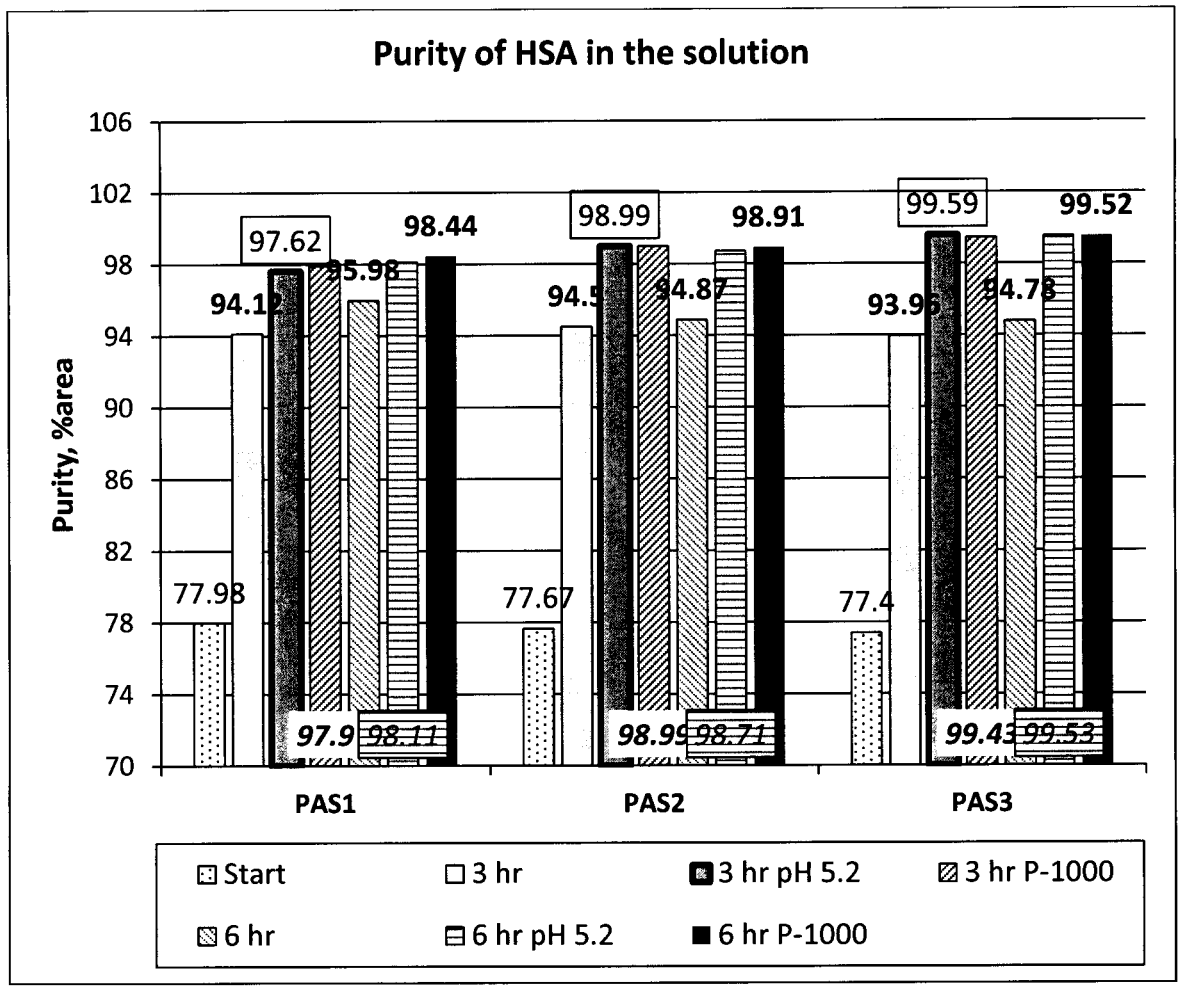
FIG. 7 shows an illustration of purities and recoveries of HSA after each purification step.
Figure 8:
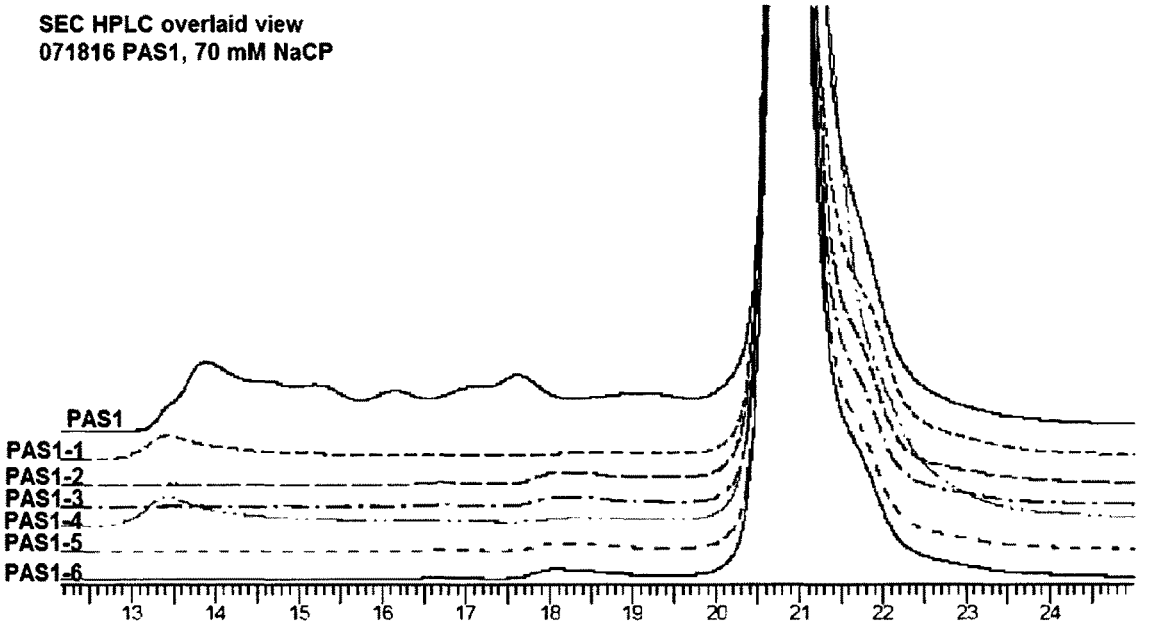
FIG. 8 shows size exclusion chromatography chromatograms of the PAS1 samples after each treatment step.

The total protein concentration (071316 SPTFF-2) was assumed to be approximately 1.8 mM. The ratios of NaCP/total protein were 39, 50 and 61, for 70, 90 and 110 mM NaCP, respectively. Sample preparation is summarized in Tables 8 and 9. The result of the experiment was expressed as purity of HSA based on SEC HPLC analysis (Table 10, and FIGS. 7 and 8). As shown in Table 9 (also see results in FIG. 7), PAS1 is in 70 mM NaCP, PAS2 in 90 mM NaCP and PAS3 in 110 mM NaCP. FIG. 9 shows that as the concentration of NaCP increased, the band at 70 kDa disappeared (lanes 8 and 10). A comparison between before and after pH adjustment followed by filtration with filter aid showed the removal of aggregates and higher molecular weight impurities.

TABLE 8

Experimental design for three different NaCP concentrations to a fixed total protein concentration.

| Sample code | Sample sub-number | Description |
| --- | --- | --- |
| 071816 PAS# | — | 071316 SPTFF-2 with 70 mM NACP |
| 071816 PAS# | 1 | PAS# after 3 hours at 65° C. |
| 071816 PAS# | 2 | Adjust pH 5.2 with PAS#-1 |
| 071816 PAS# | 3 | 0.7% P-1000 with Pas#-2 |
| 071816 PAS# | 4 | PAS# after 6 hours at 65° C. |
| 071816 PAS# | 5 | Adjust pH 5.2 with PAS#-4 |
| 071816 PAS# | 6 | 0.7% P-1000 with Pas#-5 |

TABLE 9

NaCP/total protein ratios.

| Sample | Conc of NaCP, mM | Total Protein, mM | NaCP/[TP] |
| --- | --- | --- | --- |
| 071816 PAS1 | 70 | 1.8 | 39 |
| 071816 PAS2 | 90 | 1.8 | 50 |
| 071816 PAS3 | 110 | 1.8 | 61 |

TABLE 10

Purity of HSA.

| | Start | 3 h | 3 h pH 5.2 | 3 h P-1000 | 6 h | 6 h pH 5.2 | 6 h P-1000 |
| --- | --- | --- | --- | --- | --- | --- | --- |
| | | | sub-number | | | | |
| | — | 1 | 2 | 3 | 4 | 5 | 6 |
| 071816 PAS1 | 77.98 | 94.12 | 97.62 | 97.90 | 95.98 | 98.11 | 98.44 |
| 071816 PAS2 | 77.67 | 94.50 | 98.99 | 98.99 | 94.87 | 98.71 | 98.91 |
| 071816 PAS3 | 77.40 | 93.96 | 99.59 | 99.43 | 94.78 | 99.53 | 99.52 |

Conclusion

As the ratio of NaCP vs total protein (TP) increased, the purity of HSA increased. The highest purity was obtained from 110 mM NaCP (NaCP/TP ratio: 61). HSA purity increased from 77-78% to 94% after pasteurization of the solution. By adjusting pH to 5.2 after pasteurization, HSA purity was shown to be more than 98%. Pasteurization may be completed in as quickly as 3 hours. The addition of filter aid also increased purity.

Example 4

Two Different pHs During Pasteurization

Two solutions with 90 mM NaCP were prepared. The solutions were then adjusted to pH 7 and 7.3, followed by pasteurization heat treatment at 60-65° C. Pasteurization was stopped after 6.5 h, the samples were collected, and then adjusted to pH 5.2 using citric acid. A portion of the pH-adjusted samples were collected, the remaining samples were centrifuged and the supernatants were collected and then adjusted to 7. The purity of HSA was assessed after each stage, i.e. after pasteurization, first pH adjustment to 5.2, and second pH adjustment to 7.

Figure 10:
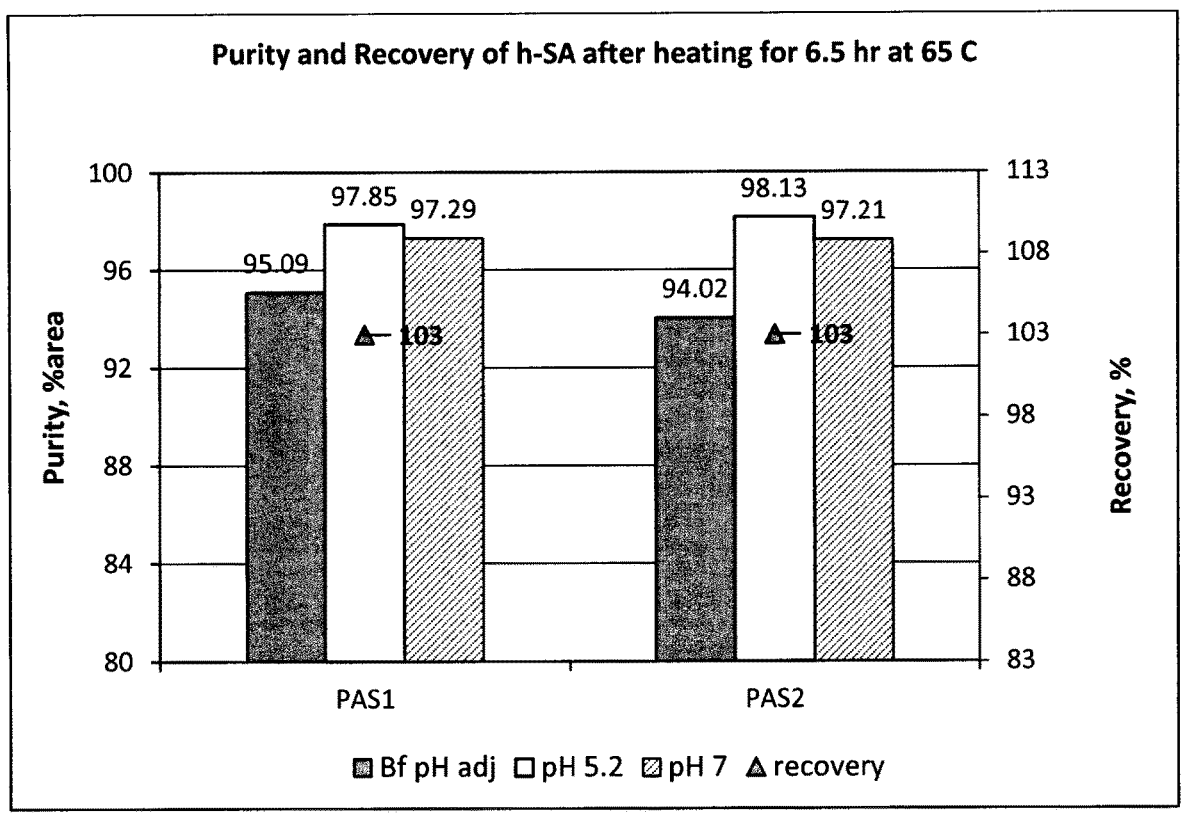
FIG. 10 shows purities of HSA after each treatment.
Figure 11:
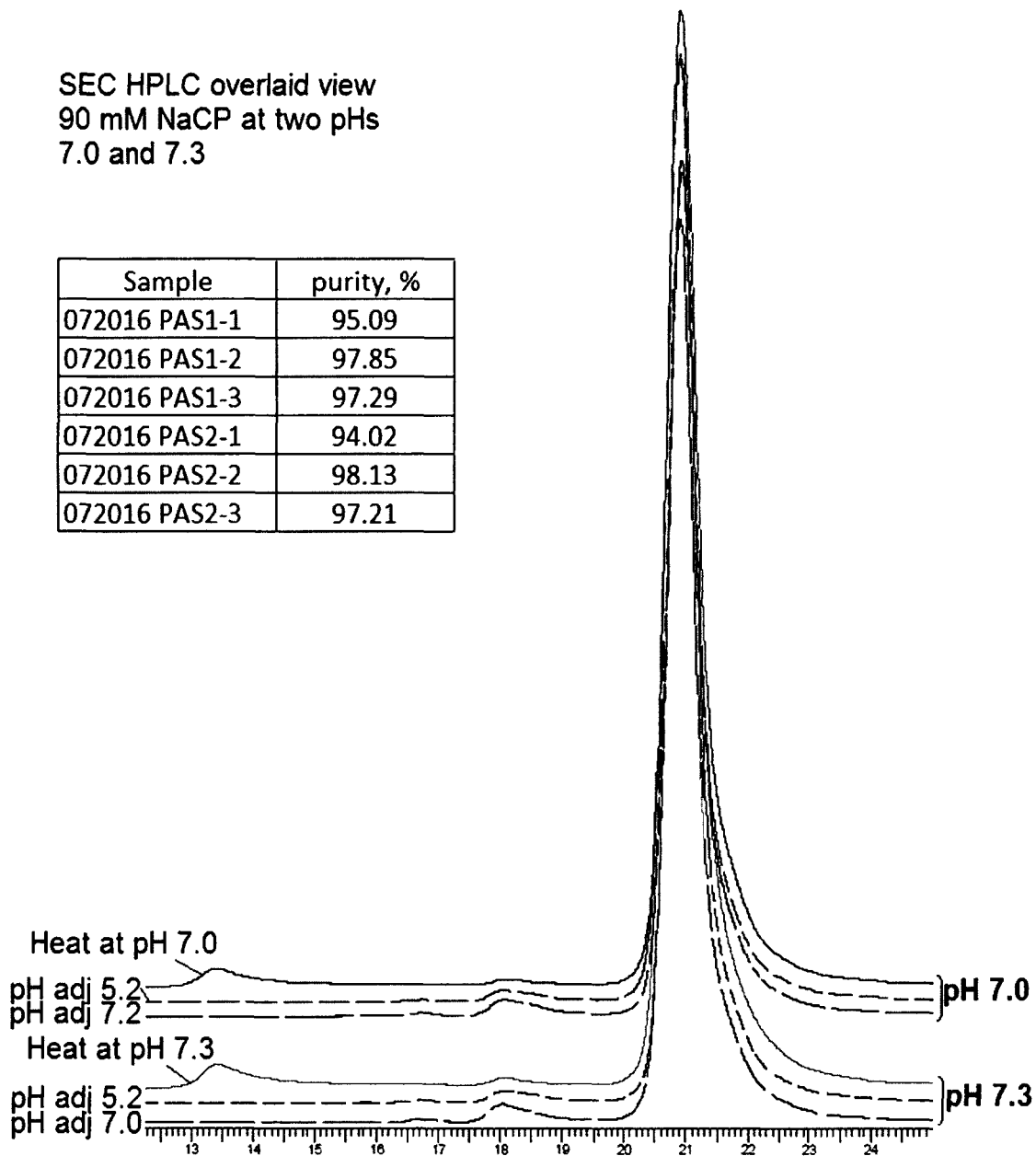
FIG. 11 shows size exclusion chromatography chromatograms overlay view.

The ratio of NaCP/TP was 50 for both samples. Sample preparation is summarized in Table 11. The result of the experiment was expressed as purity of HSA based on SEC HPLC analysis (Table 12, and FIGS. 10 and 11). Recovery of HSA was calculated accounting for solution dilution factors.

TABLE 11

Experimental design.

| Sample | Description |
|---|---|
| 072016 PAS1 | 90 mM NaCP pH 7 during pasteurization |
| 072016 PAS2 | 90 mM NaCP pH 7.3 during pasteurization |

TABLE 12

Purity of HSA as % area based on SEC HPLC analysis.

| Sample | 6.5 h | After pH 5.2 | After pH 7 | Recovery |
|---|---|---|---|---|
| 072016 PAS1 | 95.09 | 97.85 | 97.29 | 103 |
| 072016 PAS2 | 94.02 | 98.13 | 97.21 | 103 |

Conclusion

Higher pH during pasteurization yielded slightly higher purity of HSA. However, when the pH of the supernatant of the centrifuged solution was adjusted back to 7, purity dropped. The recovery of HSA is 100%. T is found that pasteurization time of up to 6.5 hour did not cause a drop in purity.

Example 5

Three Different Total Protein Concentrations and Four Different NaCP/TP Ratios

Six solutions were prepared as shown in Table 13. The starting solution was diluted to a half and a quarter so that the testing total protein concentrations were 120, 60 and 30 mg/mL. The concentration of NaCP was determined based on total protein and the experimental design shown in Table 13. The experiment is design for investigating the effect of total protein concentration and the NaCP/TP ratio on the recovery of HSA.

TABLE 13

Experimental design.

| Sample | Description | Conc of NaCP, mM | Total Protein, mM | NaCP/[TP] |
|---|---|---|---|---|
| 072616 PAS1 | 135 mM NaCP, heated for 4 hours at 65° C. | 135 | 1.80 | 75 |
| 072616 PAS2 | 80 mM NaCP, heated for 4 hours at 65° C. | 80 | 0.9 | 89 |
| 072616 PAS3 | 67.5 mM NaCP, heated for 4 hours at 65° C. | 67.5 | 0.9 | 75 |
| 072616 PAS4 | 55 mM NaCP, heated for 4 hours at 65° C. | 55 | 0.9 | 61 |
| 072616 PAS5 | 40 mM NaCP, heated for 4 hours at 65° C. | 40 | 0.9 | 44 |
| 072616 PAS6 | 35 mM NaCP, heated for 4 hours at 65° C. | 35 | 0.45 | 78 |

Pasteurization was stopped after 4 h and the pH was adjusted to 5.2 using citric acid. The pH adjusted samples were centrifuged for analysis.

Figure 12:
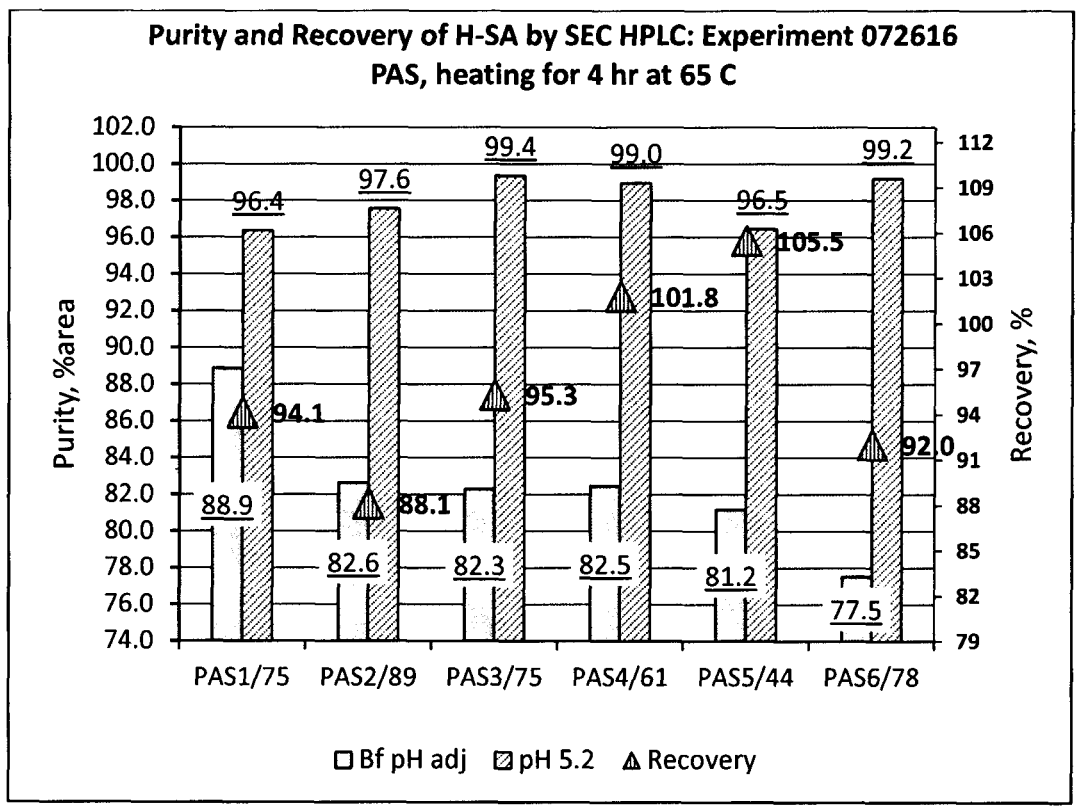
FIG. 12 shows an illustration of purities and recoveries of HSA after each purification step.
Figure 13:
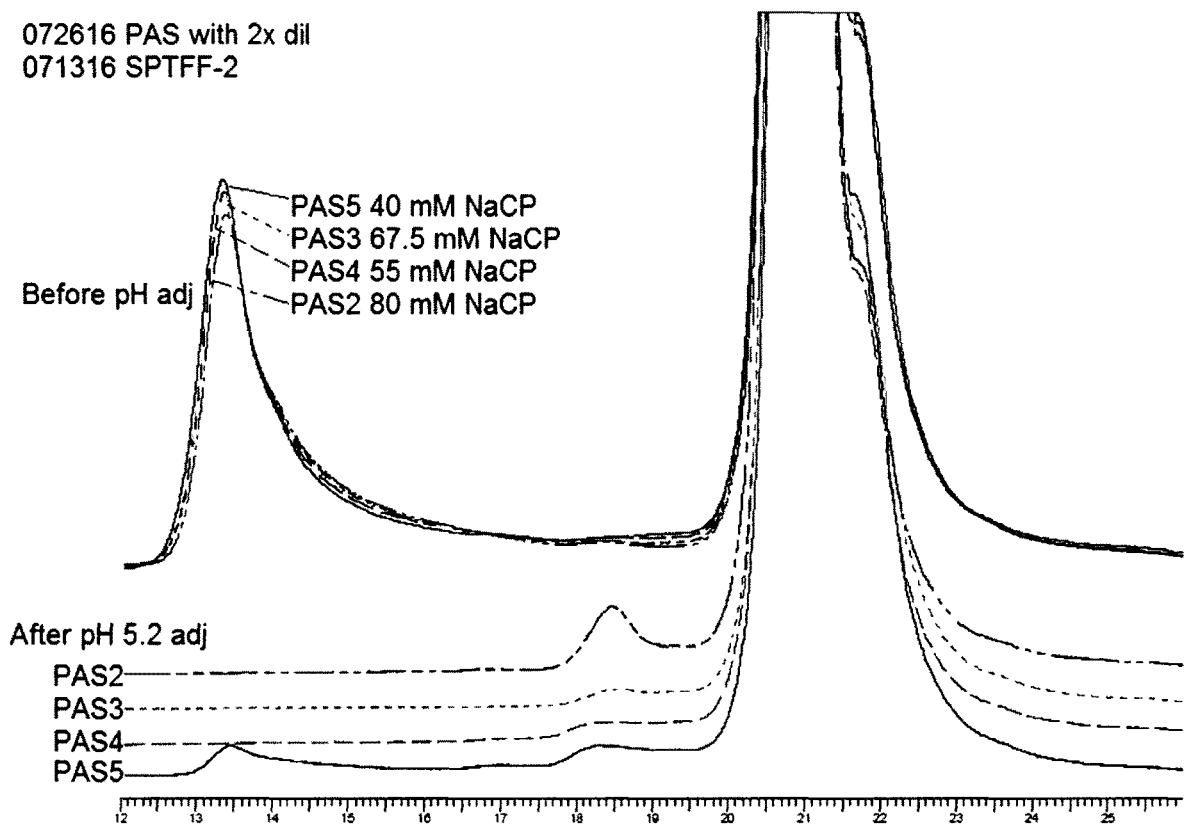
FIG. 13 shows size exclusion chromatography chromatograms of the samples after each purification step.
Figure 14:
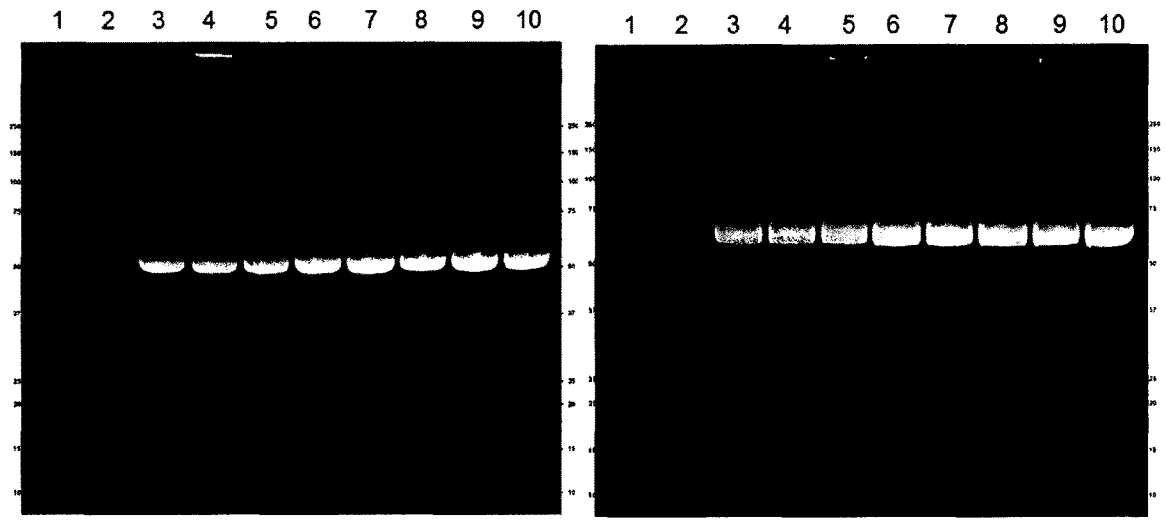
FIG. 14 shows a SDS-PAGE gel, 8% Invitrogen Gel (200 V×22 minutes).
Figure 15:
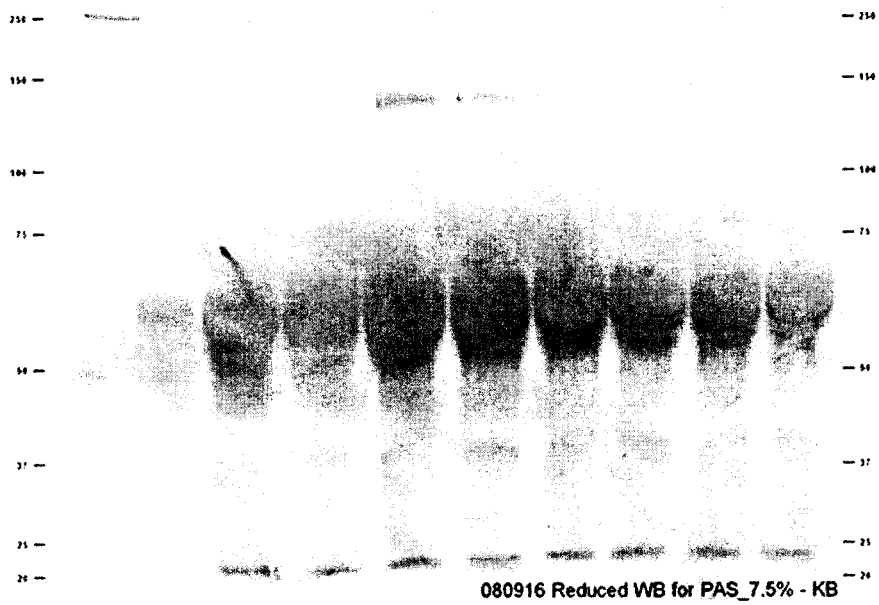
FIG. 15 shows a Western blotting for HSA.

The result of the experiment was expressed as purity of HSA based on SEC HPLC analysis (Table 14, and FIGS. 12 and 13). In FIG. 12 on the X axis, the number after PAS # is the NaCP/TP ratio. PAS1 was tested at 120 mg/mL, PAS 2-PAS5 at 60 mg/mL and PAS6 at 30 mg/mL total protein. In FIG. 13, the samples were at 60 mg/mL total protein at different NaCP concentrations. PAS2 was in 80 mM NaCP, PAS3 in 67.5 mM NaCP, PAS4 in 55 mM NaCP and PAS5 in 40 mM NaCP. Gel analysis of the samples was performed (FIG. 14). The presence of HSA was confirmed by Western blotting (FIG. 15). Recovery of HSA was calculated accounting for dilution factors.

TABLE 14

Purity of HSA as % area based on SEC HPLC analysis.

| | HSA Purity, % area | | |
|---|---|---|---|
| Sample | Before pH adj | pH 5.2 | Recovery |
| 072616 PAS1 | 88.9 | 96.4 | 94.1 |
| 072616 PAS2 | 82.6 | 97.6 | 88.1 |
| 072616 PAS3 | 82.3 | 99.4 | 95.3 |
| 072616 PAS4 | 82.5 | 99.0 | 101.8 |
| 072616 PAS5 | 81.2 | 96.5 | 105.5 |
| 072616 PAS6 | 77.5 | 99.2 | 92.0 |

Conclusion

The best result came from 60 mg/mL TP and NaCP/TP ratios between 60 and 75. When TP concentration was 120 mg/mL, the purity and recovery decreased. With 60 mg/mL TP, higher NaCP/TP ratio (89) yielded poor purity, poor recovery and more dimer. Lower NaCP/TP ratio (44) yielded poor purity but 100% HSA recovery. With 30 mg/mL TP, the purity was high but the recovery was poor. This shows that insufficient amount of NaCP may be not able to remove aggregates by precipitation. Further, surplus amount of NaCP may have caused more dimer formation.

Example 6

Two Different Total Protein Concentrations and Two Different Acids to Adjust pH

Four solutions were prepared as in Table 15. The starting solution was diluted to 60 and 80 mg/mL. The concentration of NaCP was determined based on total protein amount and NaCP/TP ratio of 72. The experiment tests for the effect of total protein concentration, process volume, impact of acid type for pH adjust past pasteurization, on the recovery of the HSA.

TABLE 15

Experimental design.

| Sample | Description | Conc of NaCP, mM | Total Protein, mM | NaCP/[TP] |
|---|---|---|---|---|
| 080916 PAS1 | 60 mg/mL TP-65 mM NaCP, heated for 4 hours at 65° C., 100 mL scale, citric acid to adjust pH 5.2 | 65 | 0.9 | 72 |
| 080916 PAS2 | 60 mg/mL TP-65 mM NaCP, heated for 4 hours at 65° C., 10 mL scale, citric acid to adjust pH 5.2 | 65 | 0.9 | 72 |
| 080916 PAS3 | 80 mg/mL TP-87 mM NaCP, heated for 4 hours at 65° C., 10 mL scale, citric acid to adjust pH 5.2 | 87 | 0.9 | 72 |
| 080916 PAS4 | 80 mg/mL TP-87 mM NaCP, heated for 4 hours at 65° C., 10 mL scale, phosphoric acid to adjust pH 5.2 | 87 | 0.9 | 72 |

Pasteurization was stopped after 4 h and the pH of the solution was adjusted to 5.2 using citric acid or phosphoric acid. The pH adjusted samples were mixed with the filter aid (P-1000). The analytical samples were centrifuged, and the bulks were filtered through a depth filter for the 100 mL scale sample and glass fibre filter for 10 mL scale samples.

The 100 mL scale sample became 131 mL after addition of P-1000. The mixture was filtered over a pre-wet K700 (60 mm, installed on a Pendo Tech filtration vessel. Pre-wet with WFI. Membrane holds up volume 8 mL). The filtrate was collected after applying pressure at 10 psi until 80 mL filtrate was collected, and then 35 psi for the rest of the volume. The filter was chased by 16 mL of 30 mM sodium citrate, pH 5.2.

The 10 mL scale samples were loaded on a pre-wet glass fibre filter (with WFI). Each filtration was performed after loading 8 mL of the sample. Chasing was not performed.

Both depth filtration and glass fibre filtration yielded a clear solution.

Figure 16:
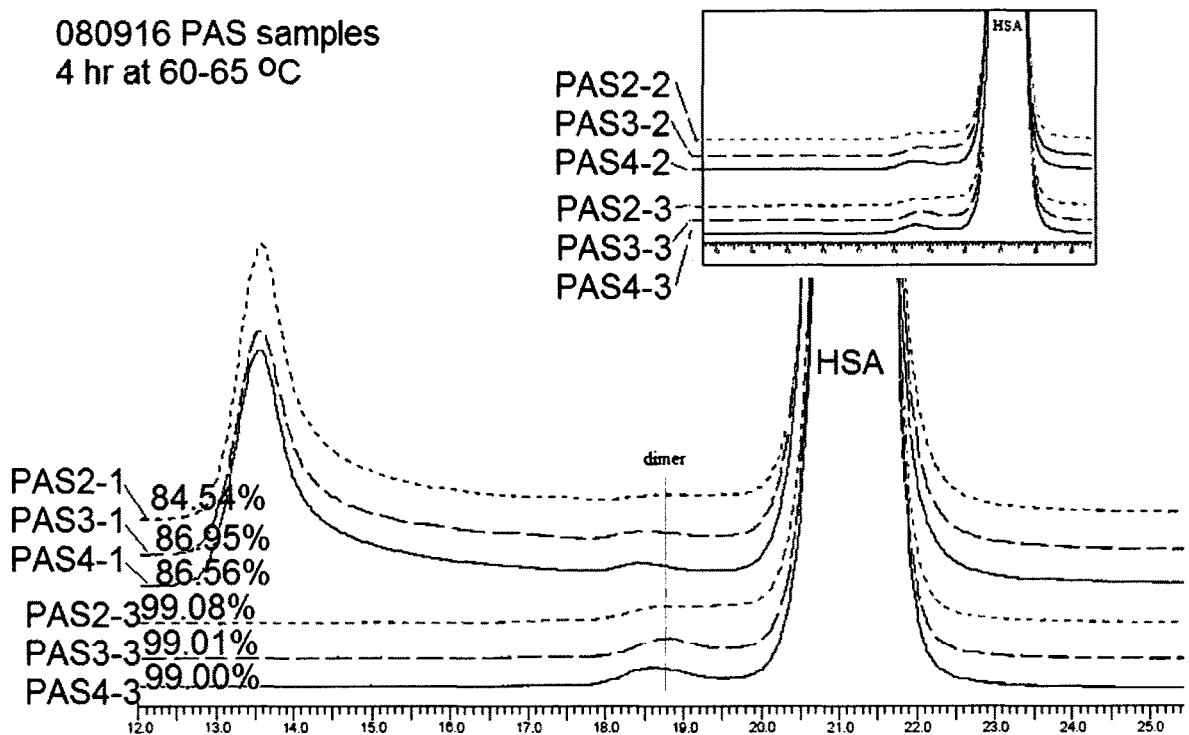
FIG. 16 shows size exclusion chromatography chromatograms of the samples after each purification step.
Figure 17:
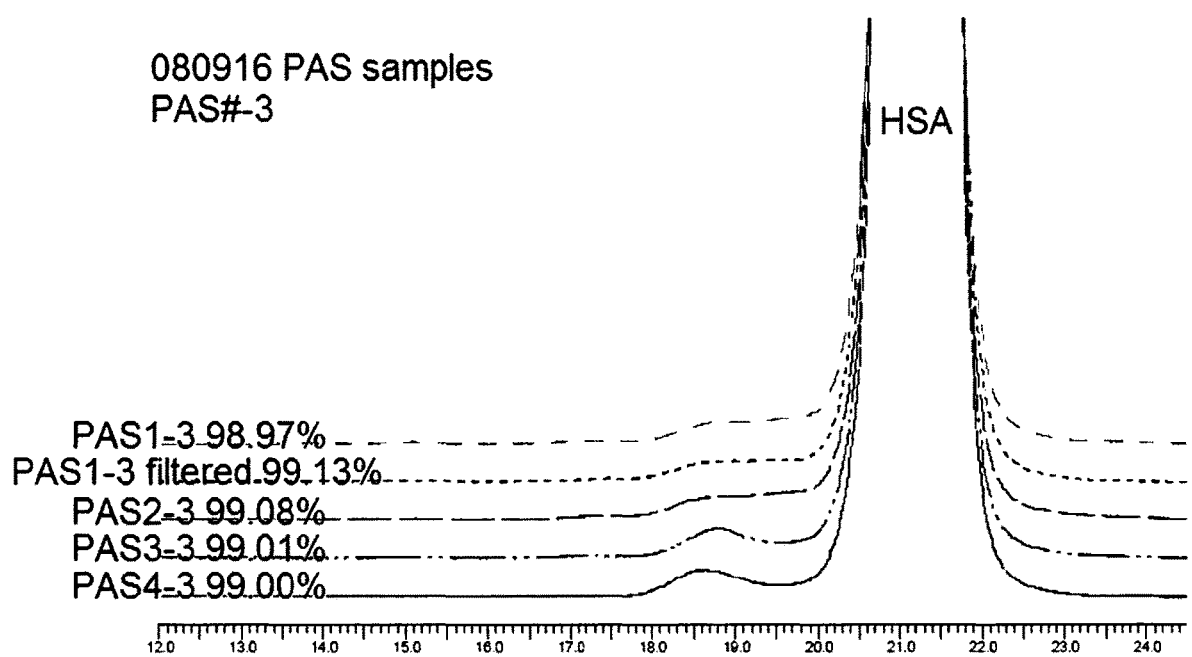
FIG. 17 shows size exclusion chromatography chromatograms of the samples.
Figure 18:
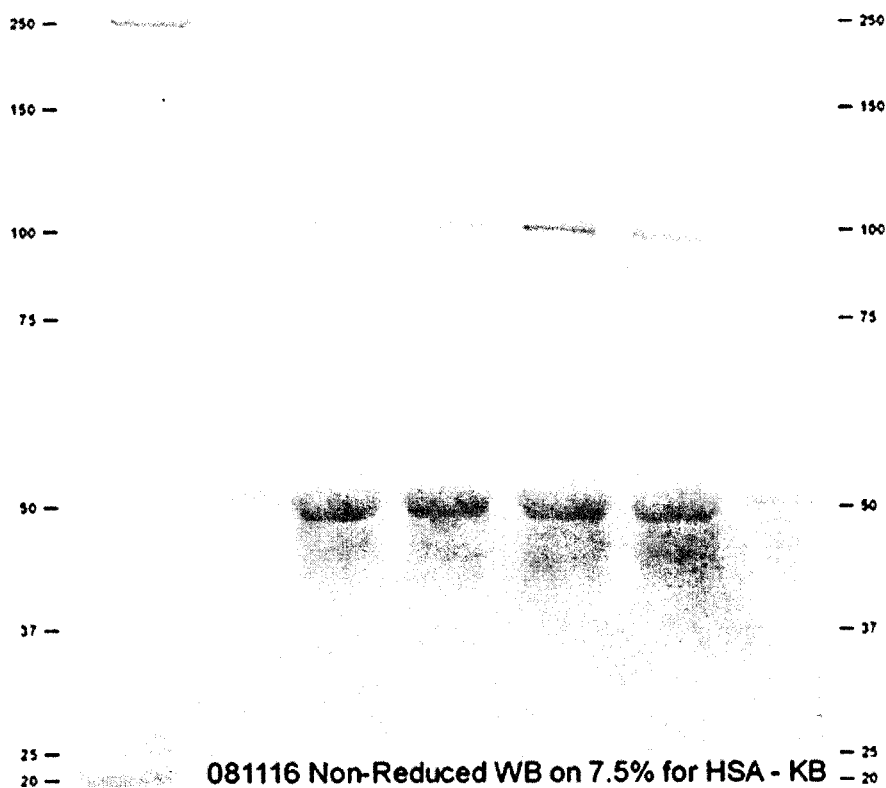
FIG. 18 shows a Western blot, 7.5% Invitrogen Gel (200 V×22 minutes) under a non-reduced condition.
Figure 20:
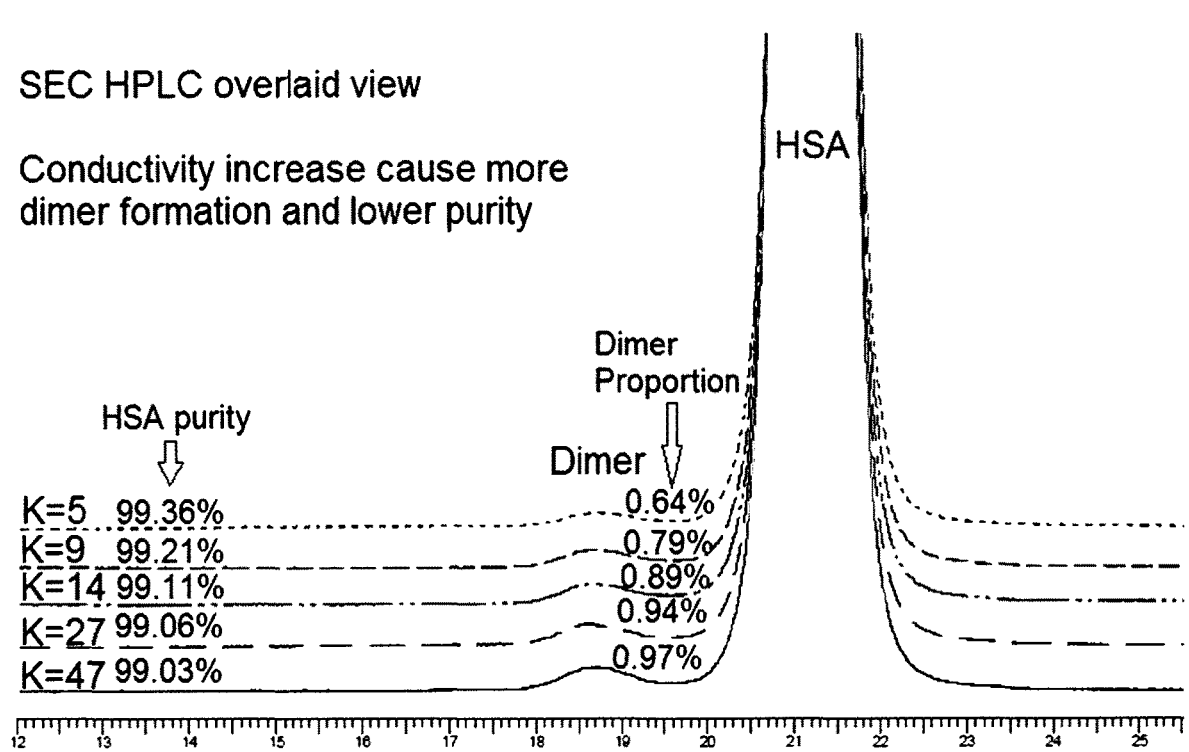
FIG. 20 shows size exclusion chromatography chromatograms of the samples from different conductivities.
Figure 21:
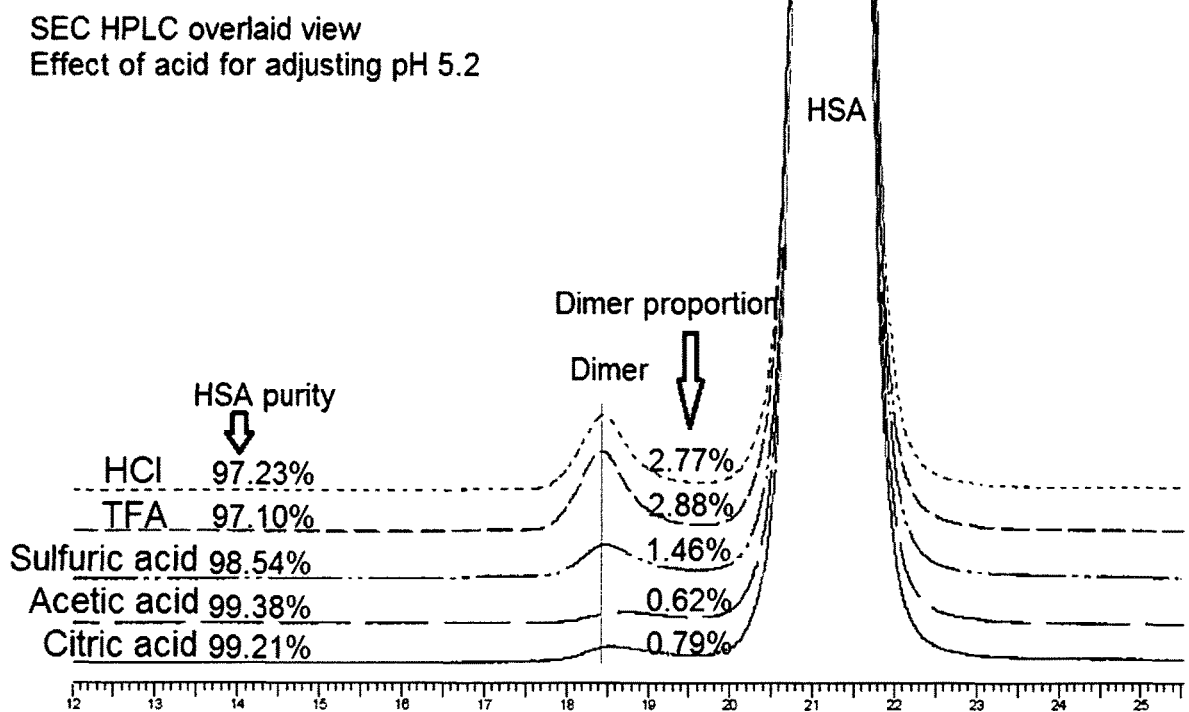
FIG. 21 shows size exclusion chromatography chromatograms of the samples pH adjusted with different acids.
Figure 22:
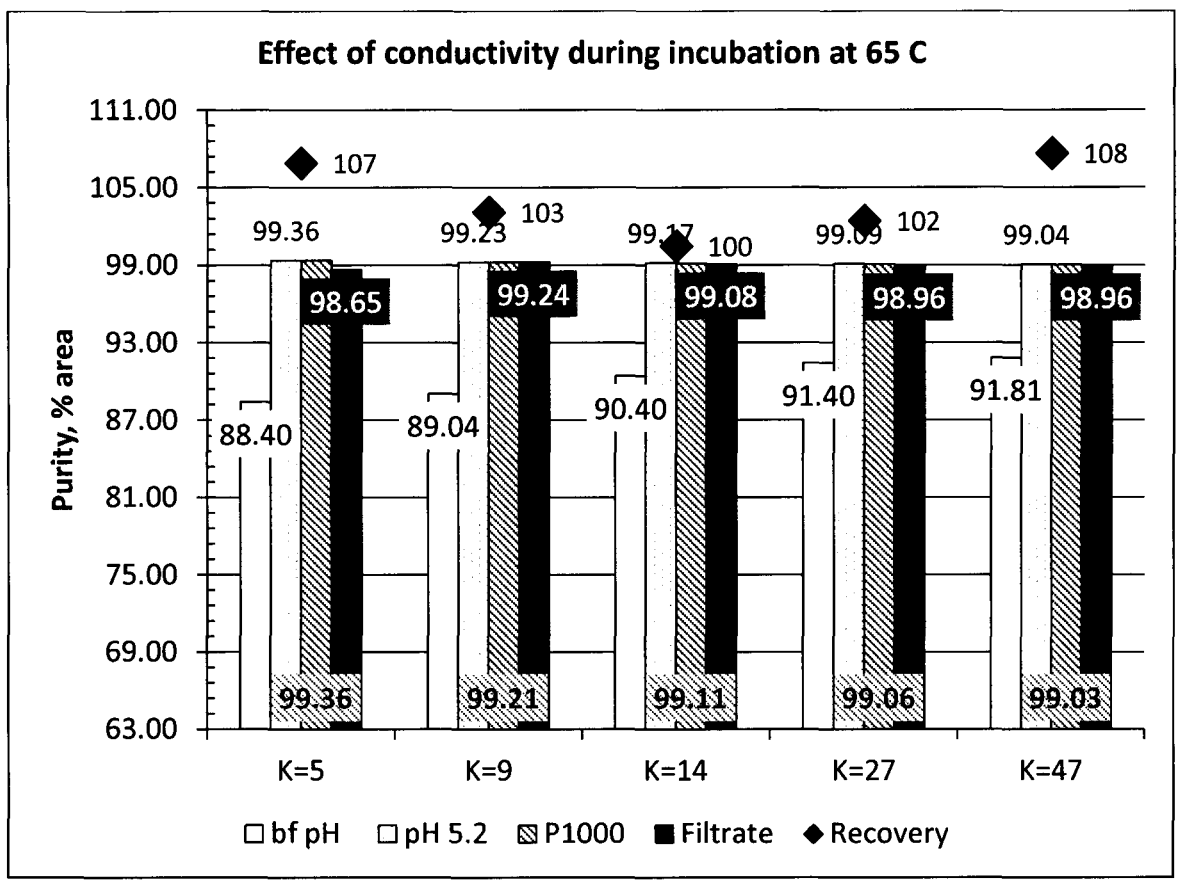
FIG. 22 shows purity and recovery profile of the samples from different conductivities.
Figure 23:
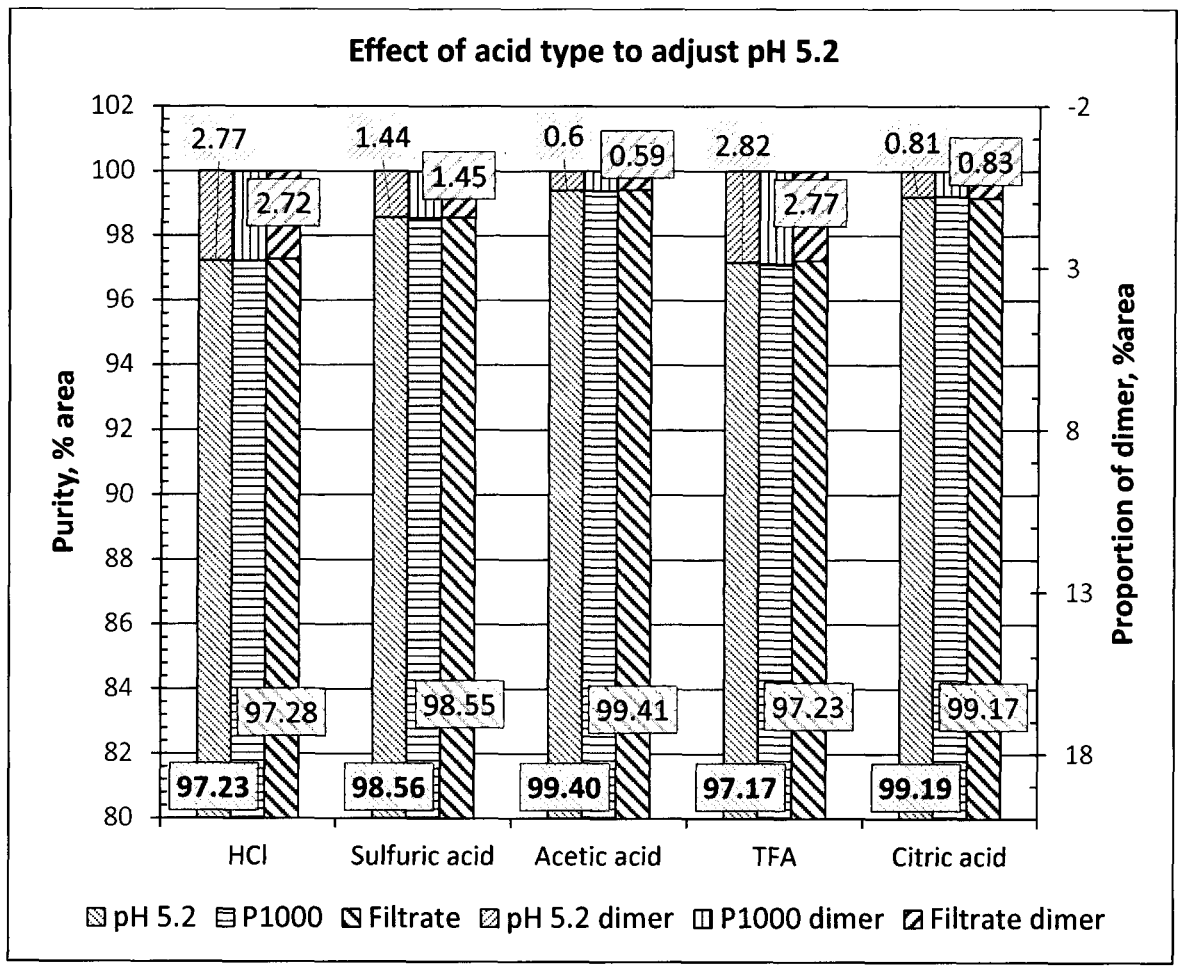
FIG. 23 shows purity and dimer formation profile of the samples from different acids used in pH adjustment.

The result of the experiment was expressed as purity of HSA based on SEC HPLC analysis (Table 16 and FIGS. 16 and 17). PAS #-1 is a sample before pH adjustment to 5.2 (FIG. 16). Insert in FIG. 16 is a chromatogram comparison of the sample: PAS #-2 represents pH adjustment to 5.2 while PAS #-3 represents the addition of P1000. The PAS2 sample is from 60 mg/mL TP and 65 mM NaCP (NaCP/TP=72) that has been treated with citric acid. The PAS3 sample is from 80 mg/mL TP and 87 mM NaCP (NaCP/TP=72) that has been treated with citric acid. The PAS4 sample is from 80 mg/mL TP and 87 mM NaCP (NaCP/TP=72) that has been treated with phosphoric acid. The PAS #-3 sample has been treated with the addition of P1000 followed by centrifugation (FIG. 17). The PAS1-3 filtered sample has been treated with the addition of P1000 followed by filtration. Recovery of HSA was calculated accounting for solution dilution factors. The resulting solutions were also analyzed by SDS-PAGE gels and Western blot in search for HSA related proteins such as dimer and oligomers. As seen in the Western blot of FIG. 18, there were bands that were not seen from the standard. The gels are shown in FIG. 19.

TABLE 16

Purity of HSA as % area based on SEC HPLC analysis.

| | Purity, % area | | | |
|---|---|---|---|---|
| Sample | Before pH adj | pH 5.2 | P-1000 | Recovery |
| 080916 PAS1 | NA | NA | 99.1 | ~93 |
| 080916 PAS2 | 84.5 | 99.0 | 99.1 | 99.6 |
| 080916 PAS3 | 87.0 | 99.2 | 99.0 | 102.7 |
| 080916 PAS4 | 86.6 | 99.0 | 99.0 | 101.1 |

Conclusion

In this Example, the NaCP/TP ratio was fixed at 72 which were between 60 and 75. PAS1 was a 10-fold scaling up of PAS2, and this 10-fold scaling up showed that there was no difference in purity and recovery. Both 60 mg/mL (PAS1 and PAS2) and 80 mg/mL TP (PAS3 and PAS4) worked well so that the TP concentration range can be set as 60-80 mg/mL TP. Both organic (PAS3) and inorganic acids (PAS4) worked for adjusting the pH without sacrificing the integrity of the product. Addition of filter aid (P1000) did not have impact on the product integrity. HSA recovery was near 100% except for the scaling up sample due to incomplete chasing of the filter.

Example 7

Conductivity Effect, Acid Influence and Filter Aid Amount

Solutions were prepared as in Table 17. The starting solution was diluted to 60 and 80 mg/mL. The concentration of NaCP was determined based on the amount of total protein and to adjust the NaCP/TP ratio to 72. The experiment tests for the effect of salt concentration (conductivity) during pasteurization, the impact of acid type, and the effect of filter aids on filterability, recovery and purity of HSA.

TABLE 17

Experimental design for pasteurization.

| Sample | Description | Conc of NaCP, mM | Total Protein, mM | NaCP/[TP] |
|---|---|---|---|---|
| 081816 PAS1 | 60 mg/mL TP-65 mM NaCP, conductivity 4.9 mS/cm, heated for 4 hours at 65° C., 10 mL scale, citric acid to adjust pH 5.2 | 65 | 0.9 | 72 |
| 081816 PAS2 | 60 mg/mL TP-65 mM NaCP, conductivity 9.4 mS/cm, heated for 4 hours at 65° C., 10 mL scale, citric acid to adjust pH 5.2 | 65 | 0.9 | 72 |
| 081816 PAS3 | 60 mg/mL TP-65 mM NaCP, conductivity 14.2 mS/cm, heated for 4 hours at 65° C., 10 mL scale, citric acid to adjust pH 5.2 | 65 | 0.9 | 72 |
| 081816 PAS4 | 60 mg/mL TP-65 mM NaCP, conductivity 26.8 mS/cm, heated for 4 hours at 65° C., 10 mL scale, phosphoric acid to adjust pH 5.2 | 65 | 0.9 | 72 |

TABLE 17-continued

Experimental design for pasteurization.

| Sample | Description | Conc of NaCP, mM | Total Protein, mM | NaCP/ [TP] |
|---|---|---|---|---|
| 081816 PAS5 | 60 mg/mL TP-65 mM NaCP, conductivity 46.8 mS/cm, heated for 4 hours at 65° C., 10 mL scale, phosphoric acid to adjust pH 5.2 | 65 | 0.9 | 72 |
| 081816 PAS6 | 60 mg/mL TP-65 mM NaCP, conductivity 4.9 mS/cm, heated for 4 hours at 65° C., 107 mL scale, Will be divided for acid and precipitation experiments (PAS6-PAS13 in Table 10) | 65 | 0.9 | 72 |
| 081816 PAS14 | 63 mg/mL TP-65 mM NaCP, conductivity 26.8 mS/cm, heated for 4 hours at 65° C., 10 mL scale, phosphoric acid to adjust pH 5.2 | 65 | 0.9 | 72 |

Samples were prepared to test for the effect of conductivity at 2, 5, 10, 20 and 50 mS/cm. Without knowing the conductivity, salt solution was added to create the conductivity. The final conductivities of the solutions were 5, 9, 14, 27 and 47 mS/cm (PAS1 to PAS5). Pasteurization was stopped after 4 h and the pH was adjusted to 5.2 using citric acid. The pH adjusted samples were mixed with P-1000 to a final concentration of 1%. The analytical samples were centrifuged, and the bulks were filtered through a depth filter.

Five 10 mL aliquots were prepared from PAS6. Each aliquot pH was adjusted to 5.2 using hydrochloric acid, sulfuric acid, acetic acid and trifluoroacetic acid, and the remaining volume was adjusted with citric acid (PAS6 to PAS10). Each pH adjusted aliquot was mixed with P1000 to a final concentration of 1%. The analytical samples were centrifuged, and the bulks were filtered through a depth filter.

Four 10 mL aliquots were prepared from PAS10. Each aliquot was mixed with filter aid as described in Table 18. The analytical samples were centrifuged, and the bulks were filtered through a depth filter.

TABLE 18

Experimental design for testing for the effect of pH adjustment and amount of filter aid.

| Sample (PAS#-2) | Description | Sample (PAS#-3) | P1000/P300 amount, % |
|---|---|---|---|
| 081816 PAS1-PAS5 | 0.5M Citric acid | 081816 PAS1-PAS5 | 1/0 |
| 081816 PAS6 | 0.5M Hydrochloric acid | 081816 PAS6 | 1/0 |
| 081816 PAS7 | 0.5M Sulfuric acid | 081816 PAS7 | 1/0 |
| 081816 PAS8 | 0.5M Acetic acid to | 081816 PAS8 | 1/0 |
| 081816 PAS9 | 0.5M Trifluoroacetic acid | 081816 PAS9 | 1/0 |
| 081816 PAS10 | 0.5M Citric acid | 081816 PAS10 | 1/0 |
| | | 081816 PAS11 | 2/0 |
| | | 081816 PAS12 | 3/0 |
| | | 081816 PAS13 | 1/1 |
| 081816 PAS14 | 0.5M Citric acid | 081816 PAS14 | 1/0 |

For filtration, the solution was loaded on a pre-wet K700 (Pre-wet the 45 mm disc with WFI and installed on a filter holder. Effective filter area was 9.6 cm² from 35 mm). The solution was filled in a 20 mL syringe with a pressure gauge.

Figure 24:
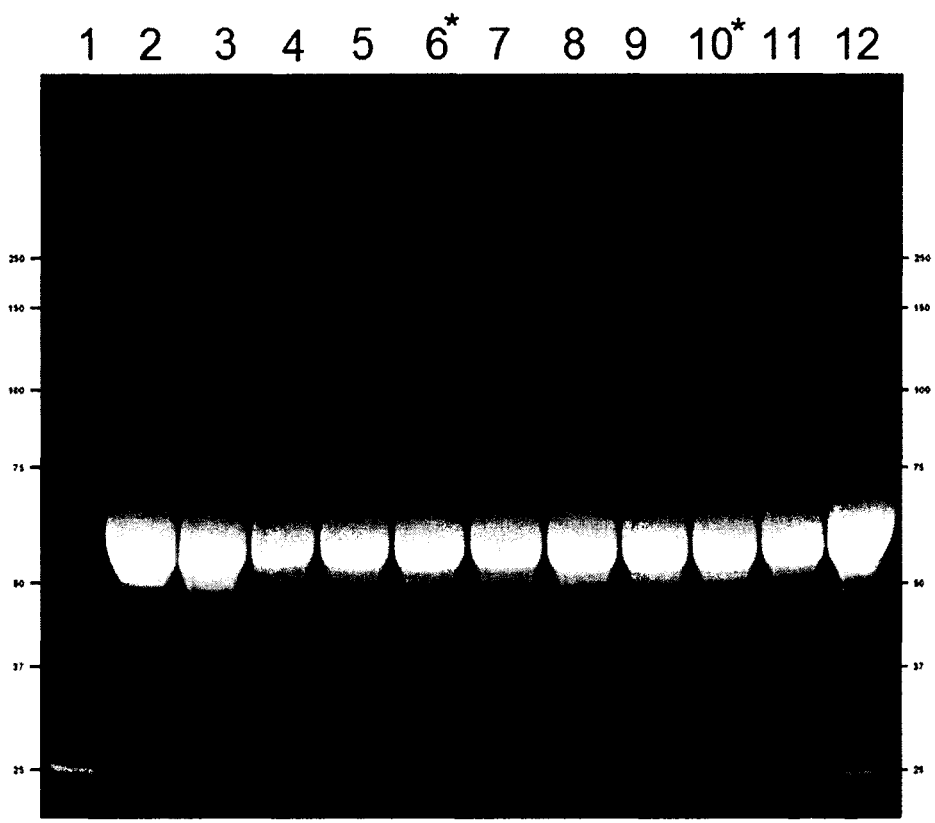
FIG. 24 shows a SGS-PAGE gel, reduced.

The result of the experiment was expressed as purity of HSA based on SEC HPLC analysis (Table 19 and FIGS. 20, 21, 22 and 23). FIG. 24 showed the protein profile after different acid treatments, with the acid treated samples in lanes 6 to 10. Recovery of HSA was calculated accounting for solution dilution factors.

TABLE 19

Purity of HSA in % area based on SEC HPLC analysis.

| | Purity, % area | | | Recovery |
|---|---|---|---|---|
| Sample | Before pH adj | pH 5.2 | Filter aid | By centrifugation |
| 081816 PAS1 | 88.40 | 99.36 | 99.36 | 107 |
| 081816 PAS2 | 89.04 | 99.23 | 99.21 | 103 |
| 081816 PAS3 | 90.40 | 99.17 | 99.11 | 100 |
| 081816 PAS4 | 91.40 | 99.09 | 99.06 | 102 |
| 081816 PAS5 | 91.81 | 99.04 | 99.03 | 107 |
| 081816 PAS6 | 86.56 | 97.23 | 97.23 | 101 |
| 081816 PAS7 | | 98.56 | 98.54 | 101 |
| 081816 PAS8 | | 99.40 | 99.38 | 101 |
| 081816 PAS9 | | 97.17 | 97.10 | 100 |
| 081816 PAS10 | | 99.19 | 99.21 | 101 |
| 081816 PAS11 | | | 99.20 | |
| 081816 PAS12 | | | 99.23 | |
| 081816 PAS13 | | | 99.16 | |
| 081816 PAS14 | 91.76 | 99.11 | 99.04 | 95 |

Conclusion

The NaCP/TP ratio used in this Example was 72. As conductivity increased, dimer formation increased and HSA monomer proportion decreased. Both inorganic and organic acid worked well to precipitate NaCP and co-precipitation of impurities. It is found that acid type influences purity of isolated HSA; more dimer formation occurs when the acid is a strong acid. Dimer formation is founded to be in the order of trifluoroacetic acid (TFA)>hydrochloric acid>sulfuric acid>citric acid>acetic acid. Hence, adjustment of pH by acetic acid leads to the least amount of dimer formation. Once the acid precipitation completes, the amount of filter aid does not increase nor decrease purity and dimer formation.

Example 8

Pasteurization of Plasma in the Presence of NaCP—Preparation from EK1 Filtrate

The purification of HSA from the column D FT+W concentrate was successful after pasteurization of the concentrated solution at 60° C. in the presence of NaCP. Here, we investigated to see if the same success can be achieved with upstream samples. The column A FT+W was filtered over an EK1 filter, which was the first column fractionation step for the plasma fractionation. The EK1 filtrate was concentrated (082316 ILC). The partial pasteurization work with the EK1 filtrate concentrate was performed in parallel with column D FT+W concentrate for the same incubation time and at the same temperature. To the concentrated EK1 was added NaCP solution (0.6 M) to a final concentration of 104 mM followed by adjusting the pH to 7, and then heated the sample for 4 hours at 64° C. The sample was analyzed by SEC HPLC and SDS-PAGE gel. The supernatant of the pH 5.2 solution showed that the purity of HSA was 98.7% and the higher molecular weight proteins were not detectable.

Figure 25:
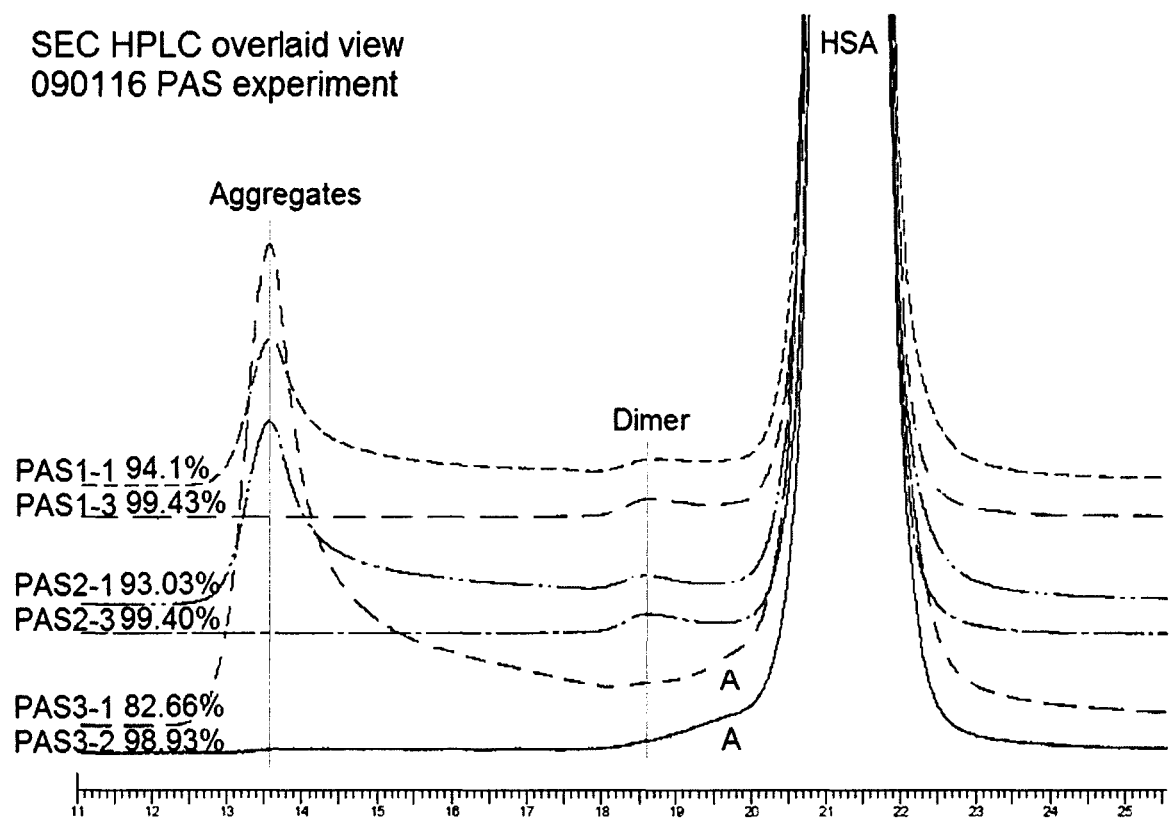
FIG. 25 shows purity, dimer and aggregate formation profile of the samples from different samples including PAS3 samples.
Figure 26:
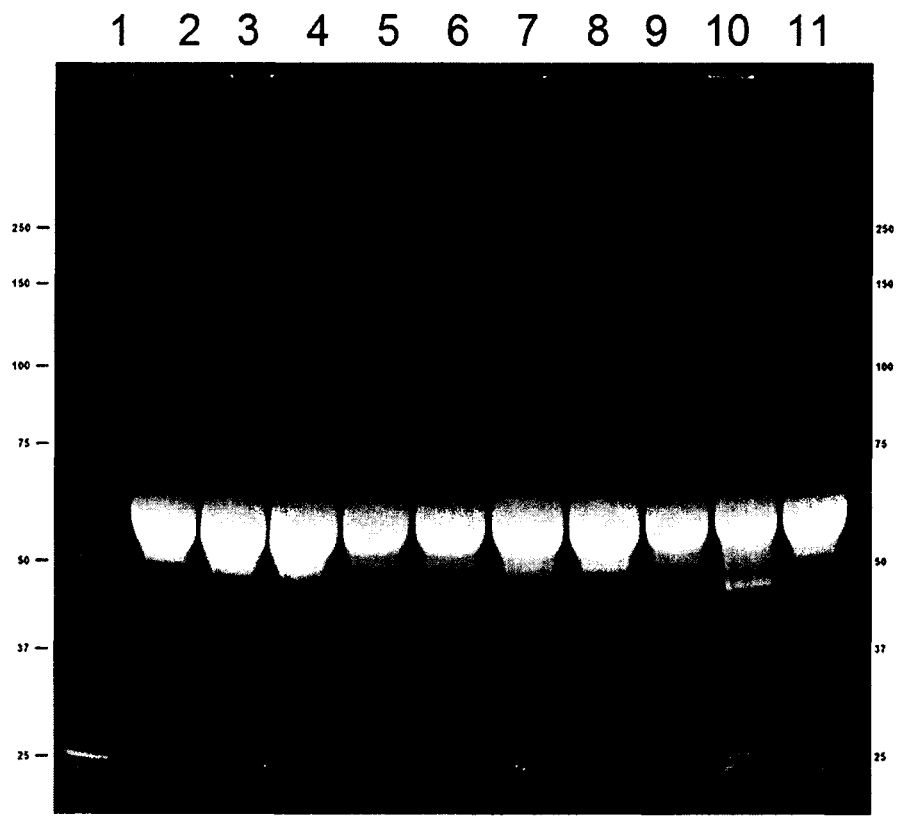
FIG. 26 shows a SDS-PAGE, 7.5% gel and under reduced condition.

The post pasteurization samples were treated with 1 M acetic acid to lower the pH to 5.2. The samples were analyzed by SEC chromatography and plotted in an overlay view (Tables 20 and 21, and FIG. 25). In FIG. 25, PAS1 and PAS2 are from column D FT+W sample and PAS3 is from the EK1 sample. PAS #-1 is the sample after pasteurization, PAS #-2 after pH 5.2, and PAS #-3 after addition of filter aid. The region marked as "A" indicates an impurity that was not observed from the other two samples. SDS-PAGE gel analysis was also performed (FIG. 26).

TABLE 20

Experimental design for pasteurization.

| Sample | Description | NaCP, mM | Total Protein, | NaCP/ [TP] |
|---|---|---|---|---|
| 090116 PAS1 | using 081216 ILC, 70 mM NaCP, pH 7 heat 4 h at 64° C. without stirring | 70 | 0.9 | 74 |
| 090116 PAS2 | using 081216 ILC, 70 mM NaCP, pH 7 heat 1 h at 64° C. stirring, 3 h without stirring | 70 | 0.9 | 74 |
| 090116 PAS3 | using 082316 ILC, 4 x dil, 104 mM NaCP, pH 7 heat 4 h at 64° C. | 104 | 0.9 | 116 |

TABLE 21

Sample description after pasteurization.

| Sample | Description | Total Protein, mg/mL | HSA purity, |
|---|---|---|---|
| 090116 PAS1-2 | Adj pH 5.2 with acetic acid | 39.9 | 99.38 |
| 090116-PAS1-3 | 1% P1000/1% P300 | 63.1 | 99.43 |
| 090116-PAS1- | 120 mL filtration over K700 | 33.1 | 99.28 |
| 090116-PAS1- | 2% P1000/1% P300, 110 mL filtration over K700 | 32 | 99.3 |
| 090116-PAS2-3 | Adj pH 5.2 with acetic acid | 42.4 | 99.4 |
| 090116-PAS2- | 230 mL filtration over K700 | 33 | 99.29 |
| 090116-PAS2-4b | 10 mL filtration over 10 μm glass fibre no chase | 54.7 | 99.31 |
| 090116-PAS3-2 | Adj pH 5.2 with acetic acid | 22.4 | 98.93 |

Conclusion

This Example shows that HSA can be purified from column A purified plasma fraction. Thus it may be feasible to recover highly pure HSA from column C FT+W, which is an intermediate fraction stage between column A and column D steps.

Example 9

Pasteurization of Plasma in the Presence of NaCP—Preparation from Column C FT+W

Column C FT+W is the second column fractionation step for the plasma fractionation. Here, the column C FT+W pool (Col C FT+W) was concentrated (091916 ILC). The partial pasteurization with the column C FT+W concentrate was performed in 300 mL scale in a jacketed glass beaker. To the concentrated column C FT+W (71 mg/mL), NaCP solution (0.6 M) was added to a final concentration of 74 mM followed by adjusting the pH to 7, and then heated for 4 hours at 64° C. The post pasteurization samples were treated with 1 M acetic acid to lower the pH to 5.2 and then 5.1. After addition of filter aid (2% P1000 and 1% P300), the mixture was filtered over a K700 depth filter. The sample was analyzed by SEC HPLC and SDS-PAGE gels.

Figure 27:
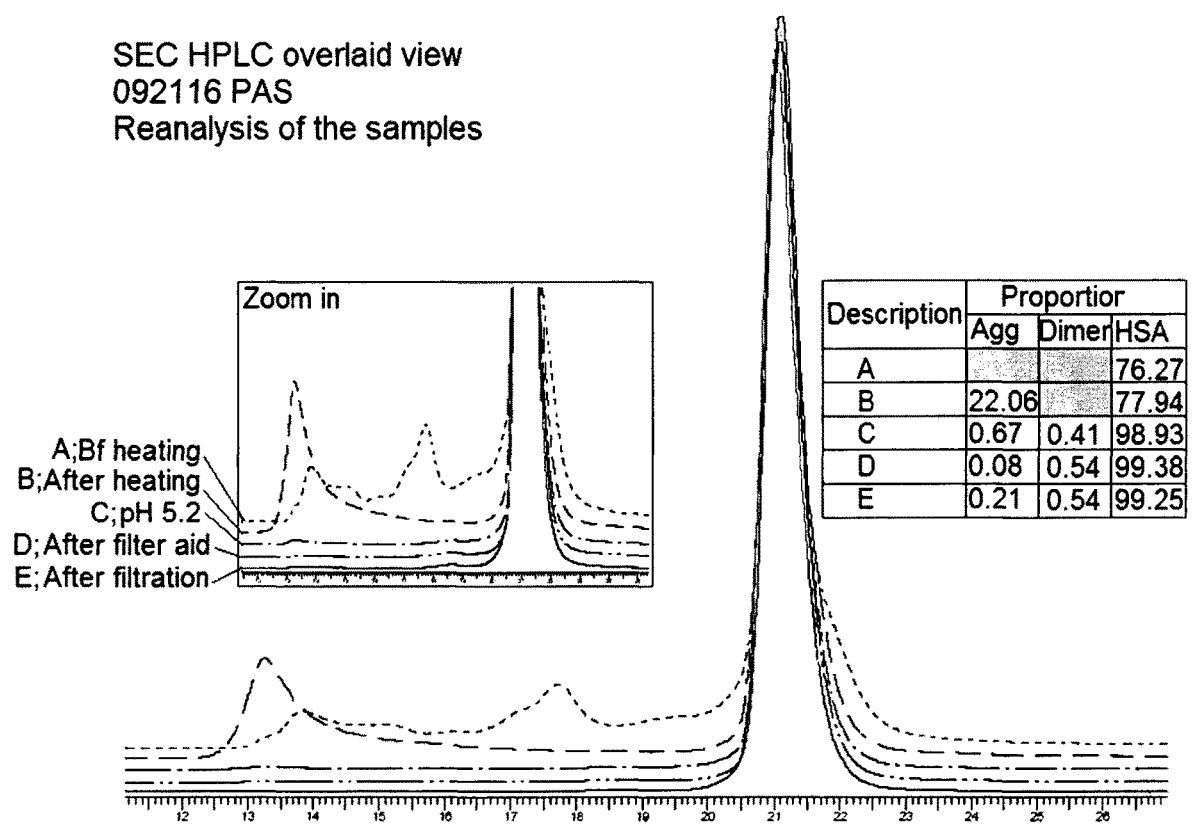
FIG. 27 shows purity, dimer and aggregate formation profile of the samples.

The sample description and the analysis result by SEC chromatography in an overlay view are listed in Table 22 and FIG. 27. SDS-PAGE gel analysis is shown in FIG. 28.

TABLE 22

Sample description and analytical results.

| Sample | Description | Total Protein, mg/mL | HSA purity, % |
|---|---|---|---|
| 092116 PAS1-1 | using 091916 ILC, 74 mM NaCP, pH 7 heat 4 h at 64° C. without stirring | 52 | 77.94 |
| 092116-PAS1-2a | Adj pH 5.2 | 36.6 | 98.93 |
| 092116-PAS1-2b | Adj pH 5.1 | 29.9 | 99.28 |
| 092116-PAS1-3 | 2% P1000/1% P300 | 30.9 | 99.38 |
| 092116-PAS1-4a | filtration over K700, greenish filtrate 230 mL | 14.3 | 99.25 |
| 090116-PAS1-4b | Centrifuged and then K700 filtrate, 235 mL | 27 | 99.29 |

Conclusion

As shown in this Example, HSA can be purified from column C purified plasma fraction. The pH of post pasteurized sample can be as low as pH 5.1 without affecting the purity of the sample. Even at the 300-mL scale, this pasteurization method can still provide >99% pure HSA. The green colour from the filtrate in PAS1-4a indicates additional purification step to be involved to further downstream process for this particular sample.

Example 10

Figure 29:
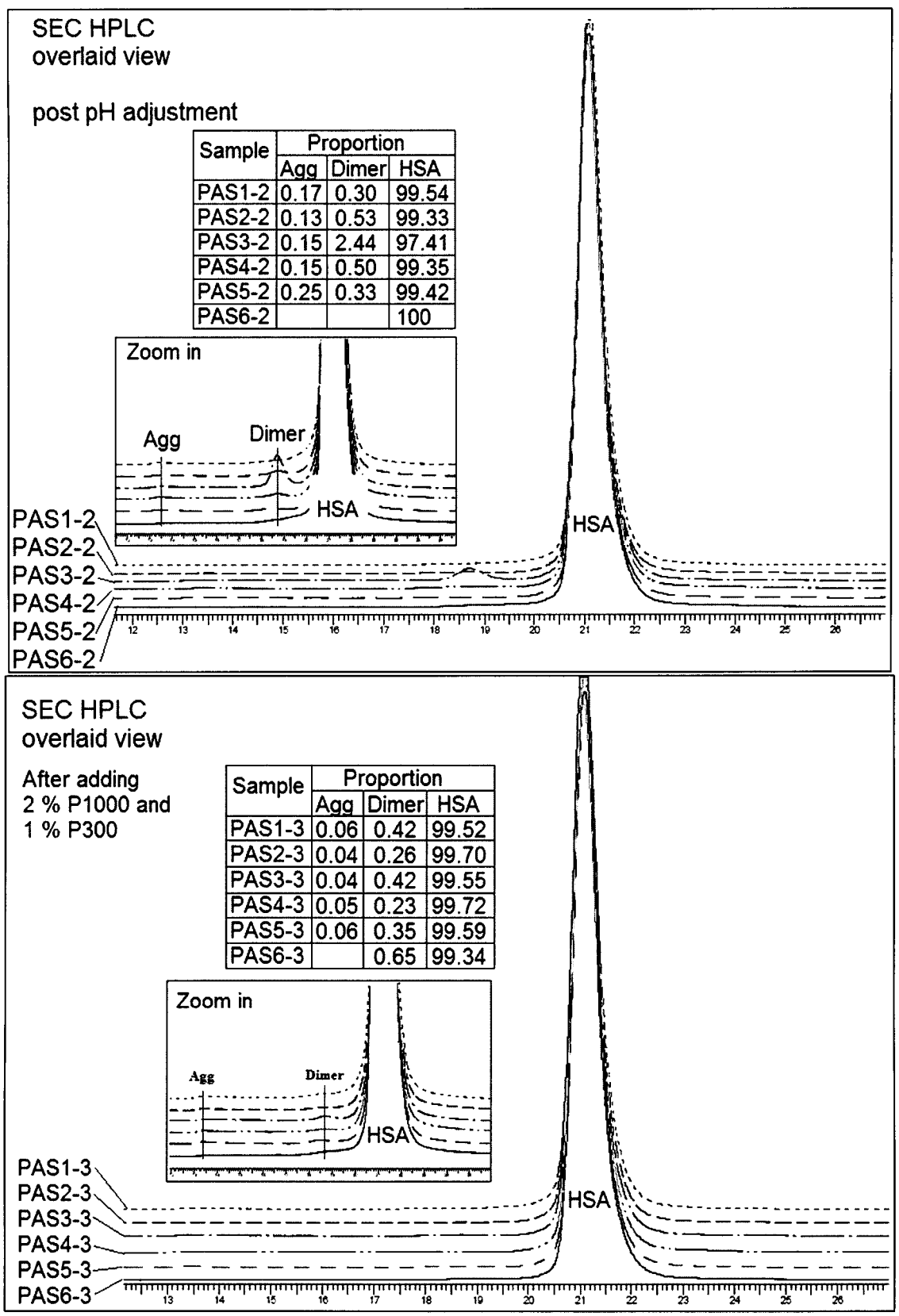
FIG. 29 shows SEC HPLC overlay views.

Pasteurization of Plasma in the Presence of NaCP—Preparation from Cryo Poor Plasma Cryo poor plasma was collected at an FDA approved collection facility. The thawed plasma has undergone partial pasteurization in parallel with column C FT+W concentrate for the same incubation time and at the same temperature. NaCP solution (0.6 M) was added to the cryo poor plasma to reach a final concentration of 80 mM, followed by adjusting the pH to 7, and then heated for 4 hours at 64° C. Post pasteurization samples were treated with 1 M acetic acid to lower the pH to 5.1. The column C FT+W concentrate was mixed with 80 to 120 mM (76 to 114 NaCP/TP ratio), and then pasteurized. The samples were analyzed by SEC HPLC and plotted in an overlay view (Table 23, and FIG. 29). As shown in Table 23, 091916 ILC and 092316 ILC were from column C FT+W. The concentration of the ILC was 53 mg/mL, and the plasma total protein concentration was estimated to be 60 mg/mL. The addition of filter aid reduced the proportion of dimer from the solution (see FIG. 29). Pasteurization with too much NaCP caused more dimer formation. Sample dilution with buffer and water do not make a difference in purity.

TABLE 23

Sample description.

| Sample | Description | NaCP/TP |
|---|---|---|
| 092716 PAS1 | using 091916 ILC, diluted with NaAc buffer, 80 mM NaCP, pH 7 heat 4 h at 64° C. | 76 |
| 092716 PAS2 | using 091916 ILC, diluted with NaAc buffer, 100 mM NaCP, pH 7 heat 4 h at 64° C. | 95 |
| 092716 PAS3 | using 091916 ILC, diluted with NaAc buffer, 120 mM NaCP, pH 7 heat 4 h at 64° C. | 114 |
| 092716 PAS4 | using 091916 ILC, diluted with water, 100 mM NaCP, pH 7 heat 4 h at 64° C. | 95 |
| 092716 PAS5 | using 092316 ILC, 80 mM NaCP, pH 7 heat 4 h at 64° C. | 100* |
| 092716 PAS6 | using 092716 CRYO, 80 mM NaCP, pH 7 heat 4 h at 64° C. | 89** |

Conclusion

This Example shows that HSA can be purified from Cryo poor plasma. Filter aid addition before filtration can reduce the dimer proportion. Dilution of starting material with buffer and water did not impact on purity. It is found that adding too much NaCP at the pasteurization step causes increased dimer formation. Thus, a NaCP/TP ratio of less than 95 is ideal.

Example 11 pH During Pasteurization in the Presence of NaCP and N-Acetyl Tryptophan

Figure 30:
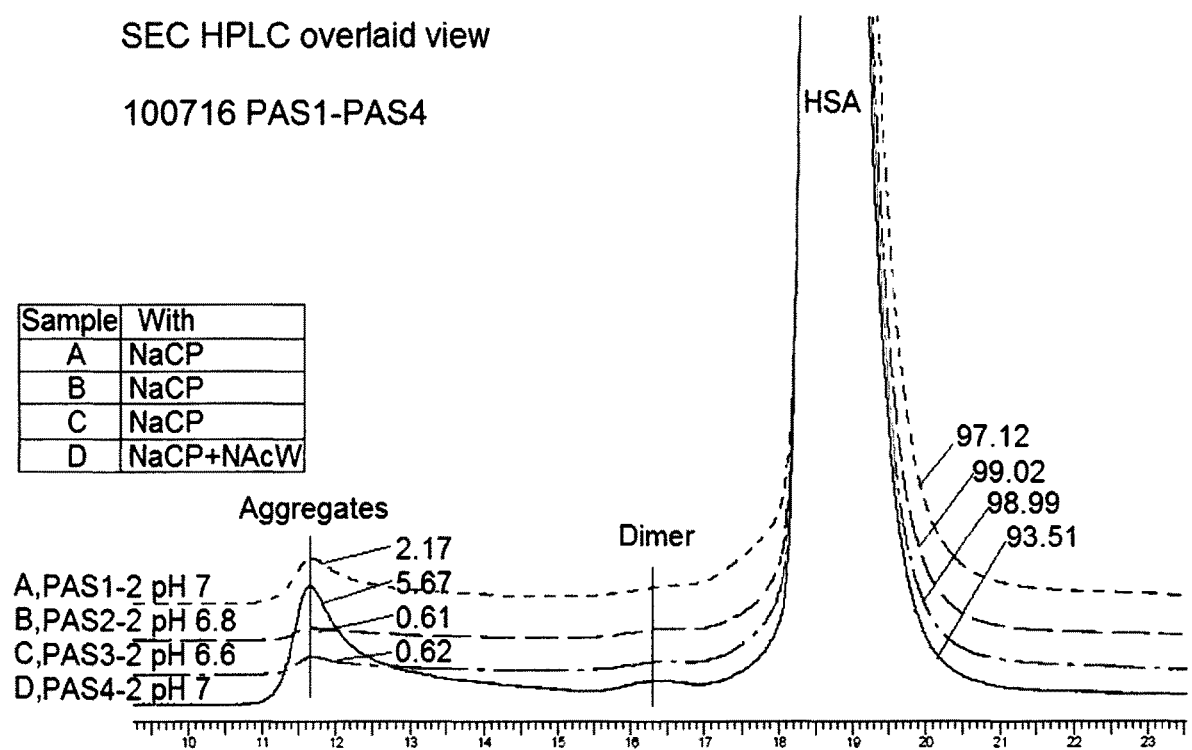
FIG. 30 shows SEC HPLC overlay views.

The pH of the sample during pasteurization was evaluated. Pasteurization in the presence of N-Acetyl Tryptophan (NAcW) in addition to NaCP was also evaluated. The pH of 7, 6.8 and 6.6 were examined. Equal amount of NaCP and NAcW was added to the pasteurization sample of a column C FT+W concentrate as described in Table 24. The amount of NaCP was added less so that the effect of pH and added NAcW could be distinguished. The samples were analyzed by SEC HPLC and plotted in an overlay view (Tables 24 and 25, and FIG. 30). The summary of the resulting purity as shown in FIG. 30 was summarized in Table 25.

TABLE 24

Sample description. 092316 ILC was from Col C FT + W.

| Sample | Description | NaCP/TP |
|---|---|---|
| 100716 | using 092316 ILC, 56 mM NaCP, pH 7 heat 4 hr at 64° C. | 70 |
| 100716 | using 092316 ILC, 56 mM NaCP, pH 6.8 heat 4 hr at 64° C. | 70 |
| 100716 | using 092316 ILC, 56 mM NaCP, pH 6.6 heat 4 hr at 64° C. | 70 |
| 100716 PAS4 | using 092316 ILC, 56 mM NaCP/56 mM NAcW, pH 7 heat 4 hr at 64° C. | 70* |

*denotes both NaCP and NAcW vs. Total protein ratio

TABLE 25

Proportion of aggregates and purity of HSA from SEC HPLC analysis

| Sample | Proportion of Aggregates | Purity of HSA |
|---|---|---|
| 100716 PAS1-2 | 2.17 | 97.12 |
| 100716 PAS2-2 | 0.61 | 99.02 |
| 100716 PAS3-2 | 0.62 | 98.99 |
| 100716 PAS4-2 | 5.67 | 93.51 |

Conclusion

The optimized pH for pasteurization is between 6.6 and 6.8. The addition of NAcW for the pasteurization step is not advised as the aggregates were not completely removed even at pH 5.1.

Example 12

As shown in the above Examples, albumin recovery and purity were maximized by a purification method that involves pasteurization under condition that specified total protein concentration and mmol NaCP per gram of total protein in the plasma. Under the disclosed method, albumin is stabilized by the presence of excess caprylate ion at near neutral pH, and impurities are selectively precipitated.

The important parameters during heat precipitation are total protein concentration and mmol NaCP per gram of total protein, as well as time, temperature, NaCP concentration, conductivity and pH. The critical quality attributes are defined as yield, purity, and percent monomer. In this Example, partially purified human plasma is treated with NaCP and heated to 60-65° C. for more than four hours. This results in the degradation of many non-target proteins while HSA remains stable. When the material is subsequently adjusted to pH 5.2, non-HSA proteins and lipid impurities precipitate and the precipitates are removed from the product stream via depth filtration.

In this Example, partially purified human plasma was concentrated to a target total protein concentration of 45-65 g/L and the resulting material was treated with NaCP (stock solution of 0.6 M, pH 7.50) to a target amount of 0.8-1.2 mmol NaCP per gram of total protein, at near neutral pH. The material was incubated at 60-65° C. for a minimum of four hours. The material was cooled to room temperature (<30° C.), adjusted to pH 5.2 with 1 M acetic acid stock solution, and filtered through a Pall Seitz K700P depth filter in the presence of Harborlite filter aid (2% w/v H900, 2% w/v H1900). The collected flow through material was a high yielding, highly pure albumin solution with low proportion of aggregates.

Example 13

Figure 31:
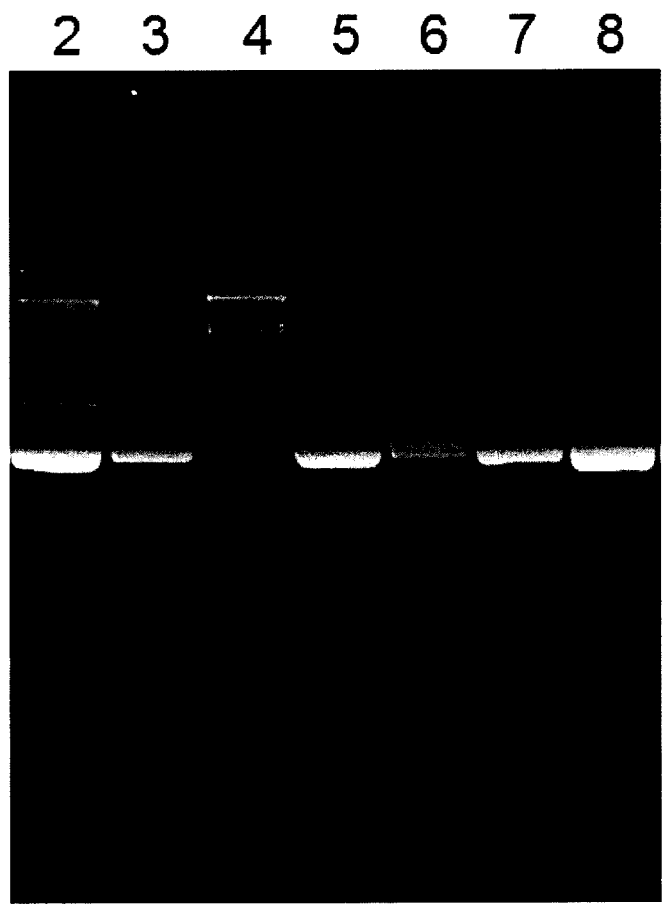
FIG. 31 shows purity of recovered HSA on a SDS-PAGE gel.

The separation of the albumin from the non-albumin phase by filtration or clarification can be carried out by depth filtration or TFF with a cassette, and preferably hollow fibre TFF. The recovery during filtration or clarification when using hollow fibre TFF is improved at pH 5.1 to 5.3. The preferred pore size, inlet pressure and value of diavolumes are shown in Table 26A and B. For hollow fibre TFF, the preferred pore size is 0.1 μm with feed flow of 8-9 L/min per m². A person skilled in the art would appreciate that feed flow between 1 and 10 L/min per m² can be used for separating albumin from non-albumin. The initial volume reduction concentration when using hollow fibre TFF is between 1× and 1.2×, preferably 1.2×, and the diavolmes is between 3 and 4, preferably 4 diavolumes. Representative relative concentration of impurities before and after pasteurization and filtration/clarification as described by the presently disclosed methods is shown in Table 27. FIG. 31 shows the purity of recovered HSA after pasteurization and filtration/clarification using hollow fibre TFF from study HSA20.

TABLE 26A

Parameters for pasteurization and filtration/clarification.

PAS1 Data

| Cascade/study | Start material | Pasteurization | | | | Filtration/Clarification | | | | |
|---|---|---|---|---|---|---|---|---|---|---|
| | | pH | K (mS/cm) | [TP] (g/L) | NCP/TP (mmol/g) | pH | Filter | Area (m2) | Pore size (μm) | Feed flow (LMM) |
| HSA5A | frozen plasma | 7.05 | 6.02 | 69.31 | 1.50 | 5.11 | Depth filter | 0.08 | 6-15 | 2.0 |
| HSA5B | frozen plasma | 7.01 | 5.74 | 61.68 | 1.43 | 5.12 | Depth filter | 0.08 | 6-15 | 2.0 |
| HSA6 | GMP 17005 Column C FT | 6.09 | 11.23 | 45.63 | 1.12 | 5.11 | Depth filter | 0.08 | 6-15 | 1.9 |
| HSA7 | GMP 17005 Column C FT | 6.80 | 5.69 | 54.63 | 1.50 | 5.11 | TFF cassette | 0.10 | 0.1 | 3.4 |
| HSA8 | GMP 17005 Column C FT | 6.90 | 4.61 | 54.46 | 1.11 | 5.10 | Depth filter | 0.08 | 6-15 | 1.9 |
| HSA9 | GMP 16077 Column C FT | 6.97 | 5.15 | 60.28 | 1.00 | 5.10 | TFF cassette | 0.10 | 0.1 | 3.5 |
| HSA10 | GMP 17019 Column C FT | 6.91 | 7.25 | 47.20 | 2.10 | 5.18 | TFF cassette | 0.10 | 0.1 | 3.5 |
| HSA11 | GMP 17005 Column C FT | 7.10 | 12.07 | 52.48 | 1.11 | 5.12 | TFF cassette | 0.10 | 0.1 | 3.5 |
| HSA12 | GMP 17005 Column C FT | 6.81 | 5.36 | 58.83 | 1.25 | 5.10 | TFF cassette | 0.10 | 0.1 | 3.5 |
| HSA14 | GMP 17036 Column C FT | 6.80 | 6.06 | 60.35 | 1.39 | 5.10 | TFF cassette | 0.10 | 0.1 | 3.5 |
| HSA15 | GMP 17005 Column C FT | 6.80 | 11.31 | 62.12 | 1.34 | 5.10 | TFF cassette | 0.10 | 0.1 | 3.5 |
| HSA16 | GMP 17036 Column C FT | 6.80 | 11.88 | 60.20 | 1.39 | 5.13 | TFF cassette | 0.20 | 0.1 | 3.5 |
| HSA17 | GMP 17036 Column C FT | 6.80 | 10.65 | 57.82 | 1.39 | 5.09 | TFF cassette | 0.20 | 0.1 | 4.3 |
| HSA18 | GMP 17036 Column C FT | 6.80 | 12.56 | 65.70 | 1.42 | 5.10 | Hollow fibre TFF | 0.02 | 0.1 | 9.0 |
| HSA19 | GMP 17036 Column C FT | 6.80 | 11.67 | 63.46 | 1.41 | 5.10 | Hollow fibre TFF | 0.02 | 0.1 | 9.0 |
| HSA20 | GMP 17019 Column C FT | 6.80 | 6.84 | 57.71 | 1.39 | 5.30 | Hollow fibre TFF | 0.02 | 0.1 | 9.0 |
| HSA21a | GMP 17019 Column CFT | 6.79 | 6.91 | 55.42 | 1.44 | 5.30 | Hollow fibre TFF | 0.09 | 0.1 | 9.0 |
| HSA21b | GMP 17019 Column C FT | 6.80 | 6.36 | 56.06 | 1.21 | 5.30 | Hollow fibre TFF | 0.02 | 0.1 | 9.0 |
| HSA22 | GMP 17036 Column C FT | 6.81 | 5.88 | 57.89 | 1.19 | 5.30 | Hollow fibre TFF | 0.09 | 0.1 | 9.0 |
| HSA23 | GMP 17005 Column C FT | 6.84 | 6.23 | 59.77 | 1.31 | 5.30 | Hollow fibre TFF | 0.09 | 0.1 | 9.0 |
| HSA24 | GMP 17005 Column C FT | 6.78 | 5.98 | 59.63 | 1.20 | 5.30 | Hollow fibre TFF | 0.09 | 0.1 | 8.0 |

TABLE 26B

Parameters for filtration/clarification. Recovery and purity of HSA after pasteurization and filtration/clarification.

PAS1 Data

| | Filtration/Clarification | | | | Result | | |
|---|---|---|---|---|---|---|---|
| Cascade/study | Target feed pressure (psi) | Target TMP (psi) | Initial conc | Diavolumes (DV) | HSA Recovery | HSA Purity | Comments |
| HSA5A | — | — | — | — | 74.42% | 99.76% | filtered in presence of filter aid |
| HSA5B | — | — | — | — | 81.65% | 89.47% | filtered in presence of filter aid |

TABLE 26B-continued

Parameters for filtration/clarification. Recovery and purity of HSA after pasteurization and filtration/clarification.

PAS1 Data

| | Filtration/Clarification | | | | Result | | |
|---|---|---|---|---|---|---|---|
| Cascade/ study | Target feed pressure (psi) | Target TMP (psi) | Initial conc | Diavol- umes (DV) | HSA Recovery | HSA Purity | Comments |
| HSA6 | — | — | — | — | 138.48% | 94.91% | filtered in presence of filter aid |
| HSA7 | 15.00 | 6.00 | 2.3x | 4 | 100.34% | 94.25% | |
| HSA8 | — | — | — | — | 85.53% | 84.10% | filtered in presence of filter aid |
| HSA9 | 8.00 | 4.50 | 1.2x | 3 | 78.00% | 85.60% | |
| HSA10 | 9.00 | 2.50 | 1.2x | 3 | 84.87% | 86.12% | |
| HSA11 | 9.00 | 4.00 | 1.2x | 3 | 87.12% | 87.73% | |
| HSA12 | 11.00 | 4.00 | 1.2x | 3 | 76.21% | 99.26% | |
| HSA14 | 11.00 | 1.00 | 1.2x | 3 | 77.80% | 101.33% | filtrate turbid after first run; cleaned membranes and repeated filtration |
| HSA15 | 11.00 | 5.00 | 1.2x | 2 | 70.30% | 88.40% | cassettes failed after 2DV |
| HSA16 | 10.00 | 2.00 | 1.2x | 3 | 77.37% | 91.62% | cassettes failed initially; cleaned and repeated next day |
| HSA17 | 10.00 | 0.00 | 1.2x | 3 | 91.08% | 99.77% | |
| HSA18 | 13.00 | 1.00 | 1.2x | 3 | 103.15% | 97.71% | |
| HSA19 | 13.00 | 1.00 | 1x | 4 | 85.99% | 91.28% | |
| HSA20 | 13.00 | 1.00 | 1x | 3 | 89.03% | 99.18% | |
| HSA21a | 13.00 | 1.00 | 1x | 4 | 80.28% | 98.71% | post ILC7 (in-line) |
| HSA21b | 13.00 | 3.00 | 1x | 4 | 80.35% | 95.71% | |
| HSA22 | 13.00 | 1.00 | 1x | 3 | 81.94% | 96.77% | post ILC7 (in-line) |
| HSA23 | 4.00 | 1.50 | 1.2x | 4 | 91.20% | 101.69% | post ILC7 (in-line) |
| HSA24 | 2.50 | 1.00 | 1.2x | 4 | 89.24% | 90.35% | post ILC7 (in-line) |

TABLE 27

Impurity of fully characterized baseline batch before and after pasteurization and subsequent filtration/clarification by TFF with a cassette.

| Impurity | Prior to PAS ug/mL | After PAS ug/mL |
|---|---|---|
| [IgA] µg/mL | 1147.05 | <3.39 |
| [IgG] µg/mL | 1167.4 | <3.4 |
| [IgM] µg/mL | 711.29 | <1.0 |
| [ApoA1] µg/mL | 6546.59 | 229.63 |
| [Ceruloplasmin] µg/mL | 31.6 | 1.17 |
| [LDL/HDL] (µg/mL) | 2676.3 | 12.6 |
| [AAT] µg/mL | 24 | <8.8 |
| C1 In ug/mL | 53 | <5.9 |
| Transferrin (ug/mL) | 2760 | 6.03 |
| Factor H (ug/mL) | 362.16 | ≤0.012 |
| Plasminogen (ug/mL) | 80.7 | <0.7 ug/ mL |
| Alpha-1-Acid-Glycoprotein (ug/mL) | 120 | <50 |
| Alpha-2 macroglobulin (ug/mL) | 1679.53 | <0.005 |
| Inter-alpha-trypsin inhibitor | present | absent |
| Transthyretin | present | absent |

The presently disclosed method shows that parameters of particular importance are total protein concentration and the ratio of NaCP to total protein in the plasma during pasteurization. The relationship between these two parameters and HSA recovery and purity across the method step are illustrated in FIG. 32 and FIG. 33, respectively.

Figure 34:
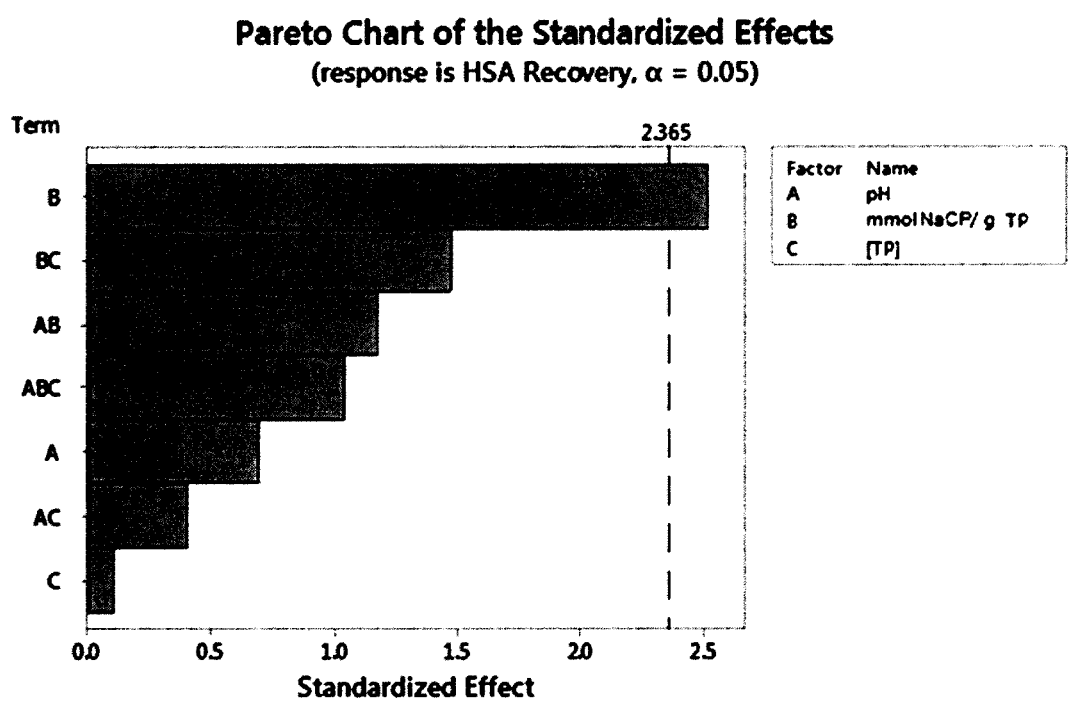
FIG. 34 shows a Pareto chart of standardized effects for HSA recovery as relating to (A) total protein concentration ([TP]) and (B) the ratio of NaCP to total protein in the material during pasteurization.
Figure 35:
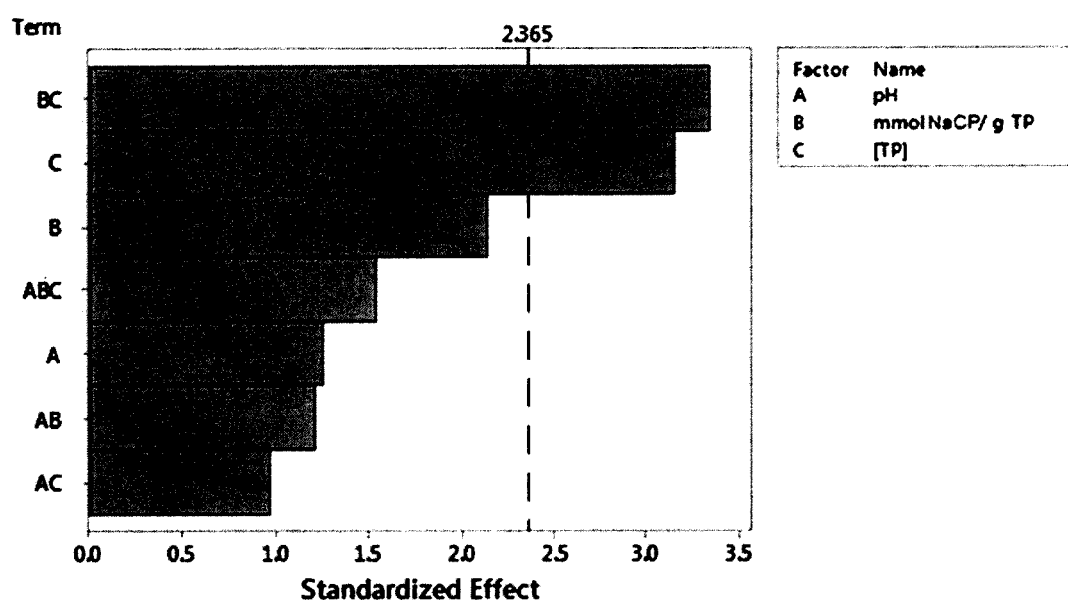
FIG. 35 shows a Pareto chart of standardized effects for HSA purity as relating to (A) total protein concentration ([TP]) and (B) the ratio of NaCP to total protein in the material during pasteurization.

Experimental analyses indicated that the recovery of HSA is related to the amount of NaCP per gram of total protein, i.e. the ratio of NaCP to total protein, in the plasma during pasteurization (see FIG. 34). HSA purity has been determined to be significantly dependent on total protein concentration, as well as the complex relationship between the total protein concentration and the NaCP to total protein ratio during pasteurization (see FIG. 35).

Figure 32:
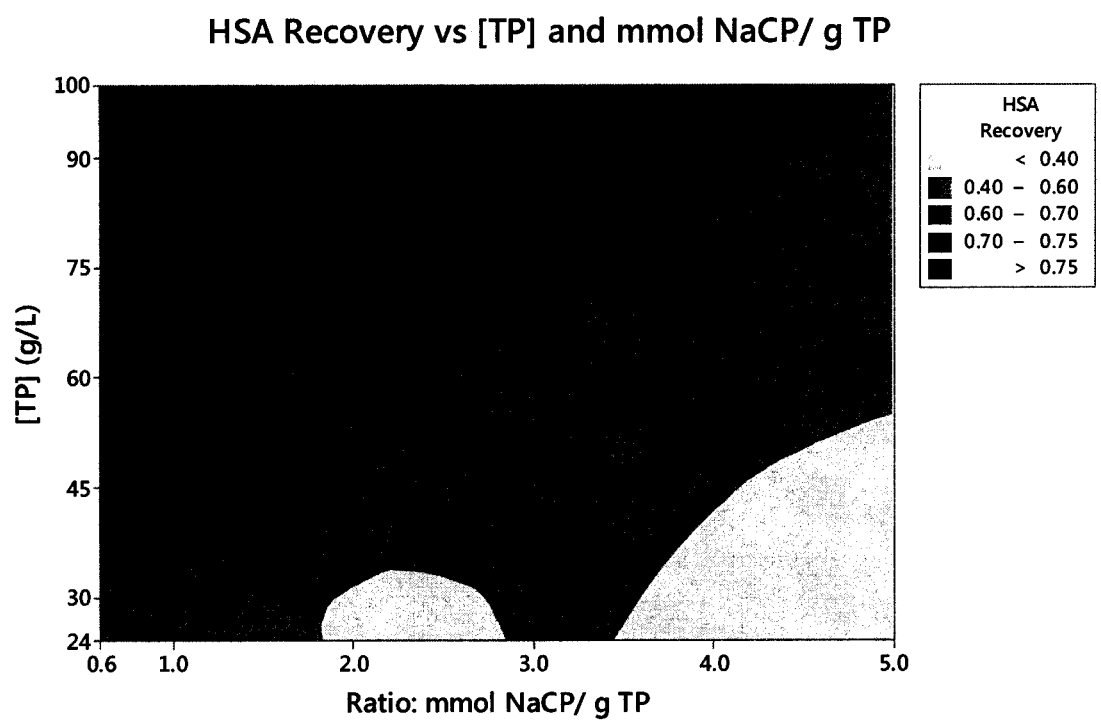
FIG. 32 shows a contour plot illustrating the effect of total protein concentration ([TP]) and the ratio of NaCP to total protein during pasteurization on HSA recovery.
Figure 33:
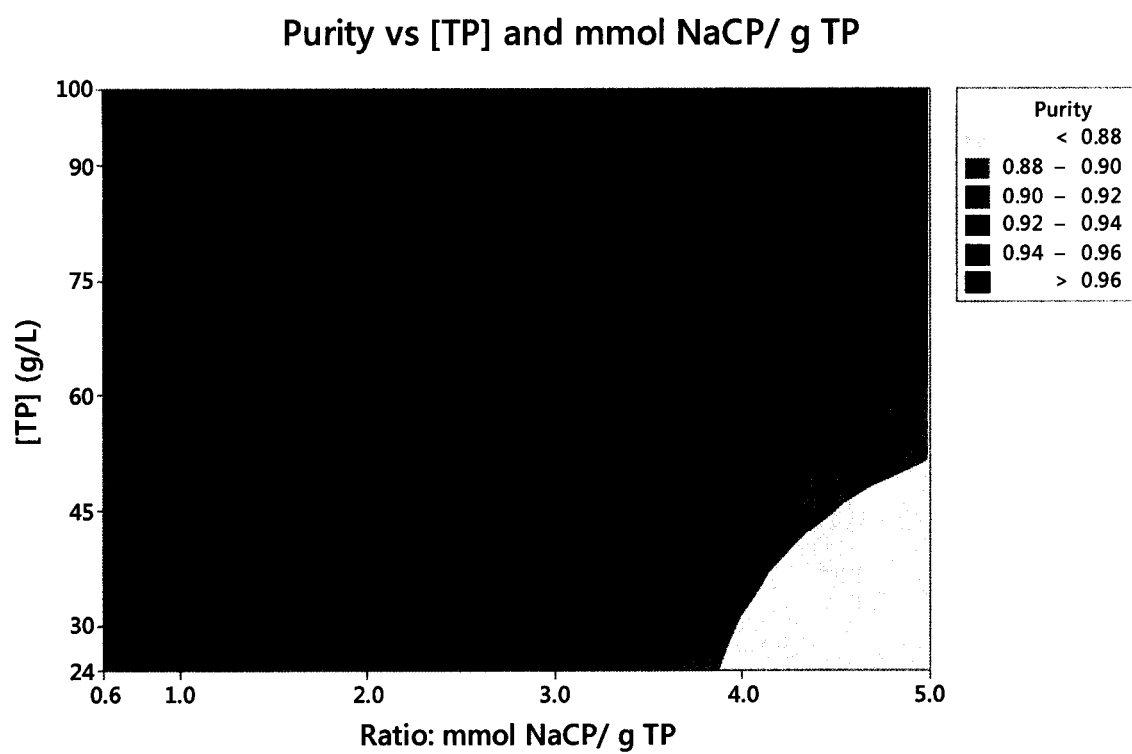
FIG. 33 shows a contour plot illustrating the effect of total protein concentration ([TP]) and the ratio of NaCP to total protein during pasteurization on HSA purity.
Figure 36:
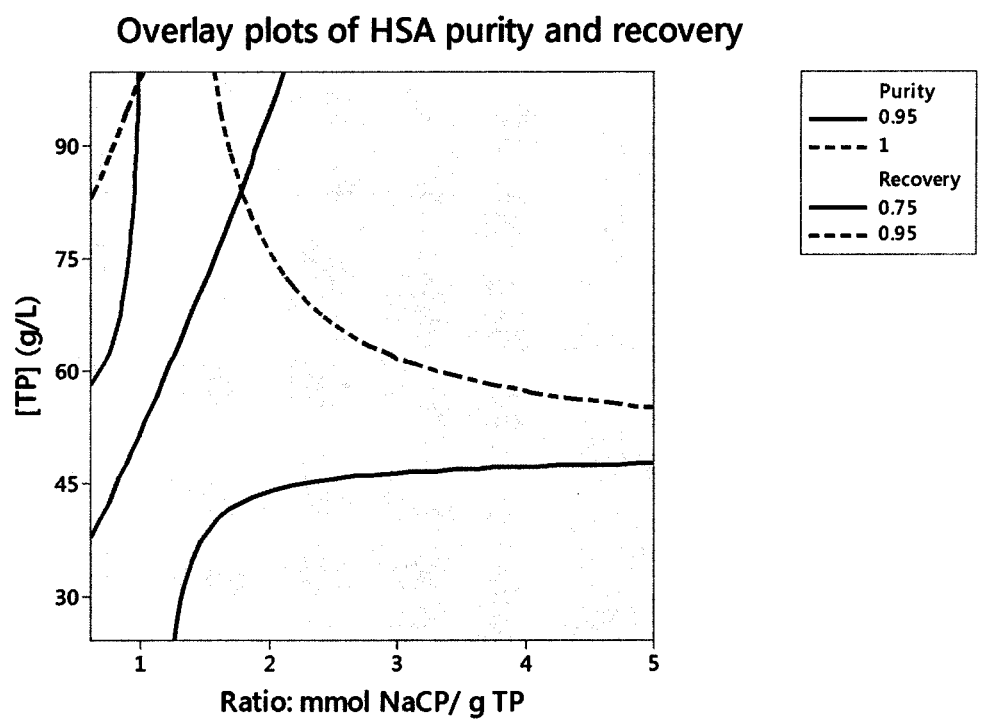
FIG. 36 shows an overlay contour plot of HSA recovery and purity indicating the optimal operating region for the parameters of focus; non-feasible region indicated in grey.

When the contour plot trends depicted in FIGS. 32 and 33 are combined into one overlaid contour plot, the optimal operating range becomes apparent for both parameters (i.e. total protein concentration of the plasma and the ratio of NaCP to total protein in the plasma during pasteurization) in order to maximize HSA recovery and purity (see FIG. 36). Operating in the lower part of that range (i.e. at a total protein concentration of 45-65 g/L and an amount of 0.8-1.2 mmol NaCP per gram of total protein) results in maximum HSA recovery and purity while ideally improving filtration performance.

While the present disclosure has been described with reference to what are presently considered to be the preferred example, it is to be understood that the disclosure is not limited to the disclosed example. To the contrary, the disclosure is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

REFERENCES

Faroongsarng D, Kongprasertkit J. 2014. The role of caprylate ligand ion on the stabilization of human serum albumin. AAPS PharmSciTech. 14(2): 465-471.
U.S. Pat. No. 2,390,074 A, December/1945, Cohn
U.S. Pat. No. 2,705,230 A, March/1955, Reid
U.S. Pat. No. 3,992,367 A, November/1976, Plan et al.
U.S. Pat. No. 4,156,681 A, May/1979, Schneider et al.
U.S. Pat. No. 5,118,794 A, June/1992, Grangeorge et al.
U.S. Pat. No. 6,022,954 A, February/2000, Dernis et al.
U.S. Pat. No. 6,504,011 B1, January/2003 van Der Laken et al.

The invention claimed is:

1. A method for purifying albumin from plasma comprising:
   (a) contacting the plasma with sodium caprylate (NaCP), wherein the amount of NaCP is between 0.8 and 1.3 mmol NaCP per gram of total protein in the plasma;
   (b) heating the plasma at a temperature between 60 and 70° C.;
   (c) separating the albumin from the non-albumin phase; and
   (d) recovering at least 75% of albumin from plasma;
   wherein the total protein in the plasma in (a) is in a concentration between 50 and 80 g/L.

2. A method according to claim 1, wherein the plasma is partially purified plasma, cryo poor plasma, plasma intermediate, solution of plasma proteins, or mixtures thereof.

3. A method according to claim 1, wherein the heating of the plasma is carried out at a pH between 6.0 and 8.0, optionally between 6.5 and 7.5, optionally between 6.7 and 7.3, optionally between 6.7 and 6.9.

4. A method according to claim 1, wherein conductivity of the plasma during heating is less than 9 mS/cm, optionally less than 5 mS/cm.

5. A method according to claim 1, wherein the heating of the plasma is carried out at a temperature between 60 and 70° C., optionally between 62 and 65° C., for a period between 0.5 and 24 hours, optionally between 2 and 12 hours, optionally between 3 and 12 hours, optionally between 4 and 6.5 hours.

6. A method according to claim 1, wherein the heating of the plasma is carried out at a pH between 6.7 and 6.9 at a temperature between 62 and 65° C. for a period of at least 4 hours, wherein the amount of NaCP is between 0.8 and 1.3 mmol NaCP per gram of total protein, wherein the total protein is in a concentration between 50 and 80 g/L.

7. A method according to claim 1, wherein the concentration of total protein is adjusted by the addition of water.

8. A method according to claim 1, wherein the separation of the albumin from the non-albumin phase comprises precipitation of non-albumin protein and lipid impurities.

9. A method according to claim 1, wherein the separation of the albumin from the non-albumin phase comprises cooling the plasma to below 30° C.

10. A method according to claim 1, wherein the separation of the albumin from the non-albumin phase comprises filtering through depth filtration, tangential flow filtration (TFF) with a cassette or hollow fibre TFF.

11. A method according to claim 1, wherein the separation of the albumin from the non-albumin phase comprises adjusting the pH of the plasma to between 4.8 and 5.4, optionally between 5.1 and 5.3.

12. A method according to claim 11, wherein the adjustment of the pH of the plasma is carried out by the addition of acid.

13. A method according to claim 12, wherein the acid comprises an organic and/or inorganic acid.

14. A method according to claim 13, wherein the organic acid is selected from citric acid, acetic acid and trifluoroacetic acid.

15. A method according to claim 13, wherein the organic acid is acetic acid.

16. A method according to claim 13, wherein the inorganic acid is selected from hydrochloric acid, sulfuric acid and phosphoric acid.

17. A method according to claim 10, wherein the separation of albumin from non-albumin comprises filtration at feed flow between 1 and 10 L/min per $m^2$, optionally between 2 and 10 L/min per $m^2$, optionally between 3 and 10 L/min per $m^2$, optionally between 8 and 9 L/min per $m^2$.

18. A method according to claim 1, wherein the method can be linearly scalable.

19. The method according to claim 10, wherein the separation of the albumin from the non-albumin phase comprises filtering through hollow fibre TFF.

* * * * *